US009689041B2

(12) United States Patent
Ye et al.

(10) Patent No.: US 9,689,041 B2
(45) Date of Patent: Jun. 27, 2017

(54) METHOD AND KIT FOR DETERMINING IN VITRO THE PROBABILITY FOR AN INDIVIDUAL TO SUFFER FROM COLORECTAL CANCER

(75) Inventors: Xun Ye, Shanghai (CN); Fei Wu, Shanghai (CN); Qinghua Xu, Zhejiang (CN); Fang Liu, Shanghai (CN); Xia Meng, Shanghai (CN); Bruno Mougin, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 610 days.

(21) Appl. No.: 14/007,439

(22) PCT Filed: Mar. 23, 2012

(86) PCT No.: PCT/CN2012/072931
§ 371 (c)(1),
(2), (4) Date: Oct. 18, 2013

(87) PCT Pub. No.: WO2012/130103
PCT Pub. Date: Oct. 4, 2012

(65) Prior Publication Data

US 2014/0057802 A1 Feb. 27, 2014

(30) Foreign Application Priority Data

Mar. 25, 2011 (CN) ................. PCT/CN2011/072155

(51) Int. Cl.
*C12Q 1/68* (2006.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 4,672,040 | A | 6/1987 | Josephson | |
| 4,683,195 | A | 7/1987 | Mullis et al. | |
| 4,683,202 | A | 7/1987 | Mullis | |
| 4,800,159 | A | 1/1989 | Mullis et al. | |
| 4,981,783 | A | 1/1991 | Augenlicht | |
| 5,234,809 | A | 8/1993 | Boom et al. | |
| 5,399,491 | A | 3/1995 | Kacian et al. | |
| 5,445,934 | A | 8/1995 | Fodor et al. | |
| 5,700,637 | A | 12/1997 | Southern | |
| 5,744,305 | A | 4/1998 | Fodor et al. | |
| 5,750,338 | A | 5/1998 | Collins et al. | |
| 5,807,522 | A | 9/1998 | Brown et al. | |
| 2004/0002082 | A1 | 1/2004 | Feinberg | |
| 2004/0033516 | A1 | 2/2004 | Mougin | |
| 2004/0265230 | A1* | 12/2004 | Martinez ............ | A61K 39/0011 424/1.49 |
| 2005/0130170 | A1 | 6/2005 | Harvey et al. | |
| 2005/0287544 | A1 | 12/2005 | Bertucci et al. | |
| 2008/0311574 | A1 | 12/2008 | Manne et al. | |
| 2011/0117083 | A1 | 5/2011 | Bais et al. | |

FOREIGN PATENT DOCUMENTS

| | | | |
|---|---|---|---|
| CN | 101068936 | A | 11/2007 |
| CN | 101111604 | A | 1/2008 |
| EP | 0 201 184 | A2 | 12/1986 |
| EP | 2 169 078 | A1 | 3/2010 |
| EP | 2 177 615 | A1 | 4/2010 |
| FR | 2 780 059 | A1 | 12/1999 |
| FR | 2 816 711 | A1 | 5/2002 |
| FR | 2 816 958 | A1 | 5/2002 |
| WO | WO 89/10977 | A1 | 11/1989 |
| WO | WO 90/01069 | A1 | 2/1990 |
| WO | WO 90/03382 | A1 | 4/1990 |
| WO | WO 90/06995 | A1 | 6/1990 |
| WO | WO 91/02818 | A1 | 3/1991 |
| WO | WO 91/19812 | A1 | 12/1991 |
| WO | WO 94/12670 | A1 | 6/1994 |
| WO | 97/45202 | A1 | 12/1997 |
| WO | WO 99/15321 | A1 | 4/1999 |
| WO | 99/35500 | A1 | 7/1999 |
| WO | WO 99/53304 | A1 | 10/1999 |
| WO | WO 99/65926 | A1 | 12/1999 |
| WO | WO 00/05338 | A1 | 2/2000 |
| WO | WO 00/71750 | A1 | 11/2000 |
| WO | WO 01/44506 | A1 | 6/2001 |

(Continued)

OTHER PUBLICATIONS

Xu et al. (Cancer Biology & Therapy, 2011, vol. 11, No. 2, p. 188-195).*
Nov. 19, 2015 Office Action issued in U.S. Appl. No. 13/698,219.
Jul. 9, 2015 Office Action issued in U.S. Appl. No. 13/698,219.
Abstract of ComBat: 'Combatting' Batch Effects When Combining Batches of Gene Expression Microarray Data, obtained from http://www.bu.edu/jlab/wp-assets/ComBat/Abstract.html on Feb. 14, 2013.
Tachibana, T., et al., "Increased Intratumor Vα24-Positive Natural Killer T Cells: A Prognostic Factor for Primary Colorectal Carcinomas," Clin. Cancer Res., Oct. 15, 2005, pp. 7322-7327, vol. 11.
Liu, J. et al., "Gene expression profiling for nitric oxide prodrug JS-K to kill HL-60 myeloid leukemia cells," Genomics, 2009, pp. 32-38, vol. 94.

(Continued)

*Primary Examiner* — Stephanie K Mummert
(74) *Attorney, Agent, or Firm* — Oliff PLC

(57) ABSTRACT

The present invention provides a method for determining in vitro, in a peripheral blood sample, the probability for an individual to suffer from a colorectal cancer, using the comparison of the amount of expression products of nucleic acids of genes of the individual to be tested with the amount of expression products of nucleic acids of the same genes obtained from a CRC group of patients constituting the positive control and with the amount of expression products of nucleic acids of the same genes obtained from a CNC group of individuals constituting the negative control; and a kit comprising specific binding partners for said expression products.

27 Claims, No Drawings

(56) References Cited

FOREIGN PATENT DOCUMENTS

| | | | | |
|---|---|---|---|---|
| WO | WO 01/44507 A1 | | 6/2001 | |
| WO | WO 02/40711 A1 | | 5/2002 | |
| WO | WO 02/090319 A1 | | 11/2002 | |
| WO | WO 02/090584 A2 | | 11/2002 | |
| WO | 2005/054508 A2 | | 6/2005 | |
| WO | WO2008063414 | * | 5/2008 | .............. C12Q 1/68 |
| WO | 2009/049228 A2 | | 4/2009 | |
| WO | 2009/126804 A2 | | 10/2009 | |
| WO | 2010/040571 A2 | | 4/2010 | |
| WO | 2010/056374 A2 | | 5/2010 | |

OTHER PUBLICATIONS

Clemson, C.M. et al., "An Architectural Role for a Nuclear Noncoding RNA: NEAT1 RNA is Essential for the Structure of Paraspeckles," Molecular Cell, Mar. 27, 2009, pp. 717-726, vol. 33.

Sheu, B., et al., "Up-regulation of Inhibitory Natural Killer Receptors CD94/NKG2A with Suppressed Intracellular Perforin Expression of Tumor-Infiltrating CD8+ T Lymphocytes in Human Cervical Carcinoma," Cancer Res., Apr. 1, 2005, pp. 2921-2929, vol. 65, No. 7.

McGilvray, R.W., et al., "NKG2D Ligand Expression in Human Colorectal Cancer Reveals Associations with Prognosis and Evidence for Immunoediting," Clin. Cancer Res., Nov. 15, 2009, pp. 6993-7002, vol. 15, No. 22.

Apr. 1, 2011 International Search Report issued in International Application No. PCT/EP2010/057843.

Apr. 1, 2011 Written Opinion of the International Searching Authority issued in International Application No. PCT/EP2010/057843.

Dec. 19, 2014 Office Action issued in U.S. Appl. No. 13/698,219.

Apr. 16, 2014 Office Action issued in U.S. Appl. No. 13/698,219.

U.S. Appl. No. 13/698,219, filed Nov. 15, 2012 in the name of Ye et al.

Killer Cell Lectin-Like Receptor Subfamily K, Member 1. Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=KLRK1>.

Killer Cell Lectin-Like Receptor Subfamily B, Member 1. Datasheet [online]. Weizmann Institute of Science, Oct. 23, 2013 [retrieved on Apr. 4, 2014]. Retrieved from the Internet: <http://genecards.org/cgi-bin/carddisp.pl?gene=KLRB1>.

Granzyme B (Granzyme 2, Cytotoxic T-Lymphocyte-Associated Serine Esterase 1). Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=GZMB>.

Related RAS Viral (R-Ras) Oncogene Homolog 2. Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=RRAS2>.

Nielsen et al., "Sequence-Selective Recognition of DNA by Strand Displacement with a Thymine-Substituted Polyamide," *Science*, Dec. 6, 1991, vol. 254, pp. 1497-1500.

Tyagi et al., "Molecular Beacons: Probes that Fluoresce Upon Hybridization," *Nature Biotechnology*, Mar. 1996, vol. 14, pp. 303/308.

Kricka, "Nucleic Acid Detection Technologies—Labels, Strategies, and Formats," *Clinical Chemistry*, 1999, vol. 45, No. 4, pp. 453-458.

Keller et al., "Non-Radioactive Labeling Procedures," and "Hybridization Formats and Detection Procedures," *DNA Probes*, 1993, pp. V and 173-253.

Chee et al., "Accessing Genetic Information with High-Density DNA Arrays," *Science*, Oct. 5, 1996, vol. 274, No. 5287, pp. 610-614.

Pease et al., "Light-Generated Oligonucleotide Arrays for Rapid DNA Sequence Analysis," *Proc. Natl. Acad. Sci. USA*, May 1994, vol. 91, pp. 5022-5026.

Cheng et al., "Preparation and Hybridization Analysis of DNA/RNA from *E. coli* on Microfabricated Bioelectronic Chips," *Nature Biotechnology*, Jun. 1998, vol. 16, pp. 541-546.

Livache et al., "Preparation of a DNA Matrix Via an Electrochemically Directed Copolymerization of Pyrrole and Oligonuclieotides Bearing a Pyrrole Group," *Nucleic Acids Research*, 1994, vol. 22, No. 15, pp. 2915-2921.

Ginot, "Oligonucleotide Micro-Arrays for Identification of Unknown Mutations: How Far From Reality?" *Human Mutation*, 1997, vol. 10, pp. 1-10.

Cheng et al., "Microchip-Based Devices for Molecular Diagnosis of Genetic Diseases," *Molecular Diagnosis*, 1996, vol. 1, No. 3, pp. 183-200.

Bustin, "Quantification of mRNA Using Real-Time Reverse Transcription PCR (RT-PCR): Trends and Problems," *Journal of Molecular Endocrinology*, 2002, vol. 29, p. 23-39.

Giulietti et al., "An Overview of Real-Time Quantitative PCR: Applications to Quantify Cytokine Gene Expression," *Methods*, 2001, vol. 25, pp. 386-401.

Irizarry et al., "Exploration, Normalization and Summaries of High Density Oligonucleotide Array Probe Level Data," *Biostatistics*, 2003, vol. 4, No. 2, pp. 249-264.

Maglott et al., "Entrez Gene: Gene-Centered Information at NCBI," *Nucleic Acids Research*, 2007, vol. 35, pp. D26-D31.

Johnson et al., "Adjusting Batch Effects in Microarray Expression Data Using Empirical Bayes Methods," *Biostatistics*, 2007, vol. 8, No. 1, pp. 118-127.

Tusher et al., "Significance Analysis of Microarrays Applied to the Ionizing Radiation Response," *PNAS*, Apr. 24, 2001, vol. 98, No. 9, pp. 5116-5121.

Ramsay, "DNA Chips: State-of-the-Art," *Nature Biotechnology*, Jan. 1998, vol. 16, pp. 40-44.

Genbank, Accession No. NM_001031700, 2000.

Genbank, Accession No. NM_016613, 2000.

Genbank, Accession No. NM_001128424, 2000.

Jul. 5, 2012 International Search Report issued in International Application No. PCT/CN2012/072931.

Oct. 1, 2013 International Preliminary Report on Patentability issued in International Application No. PCT/CN2012/072931.

* cited by examiner

SEQUENCE LISTING

<160> NUMBER OF SEQ ID NOS: 11

<210> SEQ ID NO 1
<211> LENGTH: 22743

```
<212> TYPE: DNA
<213> ORGANISM: Homo sapiens

<400> SEQUENCE: 1

ggagttagcg acagggaggg atgcgcgcct gggtgtagtt gtgggggagg aagtggctag     60

ctcagggctt caggggacag acagggagag atgactgagt tagatgagac gagggggcgg    120

gctgggggtg cgagaaggaa gcttggcaag gagactaggt ctaggggac cacagtgggg    180

caggctgcat ggaaaatatc cgcagggtcc cccaggcaga acagccacgc tccaggccag    240

gctgtcccta ctgcctggtg gagggggaac ttgacctctg ggagggcgcc gctcttgcat    300

agctgagcga gcccgggtgc gctggtctgt gtggaaggag gaaggcaggg agaggtagaa    360

ggggtggagg agtcaggagg aataggccgc agcagccctg gaaatgatca ggaaggcagg    420

cagtgggtgc agggctgcag gagggccggg agggctaatc ttcaacttgt ccatgccagc    480

agccccttt tttccagacc aagggctgtg aacccgcctg ggatgaggc ctggtcttgt    540

ggaactgaac ttagctcgac ggggctgacc gctctggccc agggtggtat gtaattttcg    600

ctcggcctgg gacggggccc aggccgggcc cagcctggtg gagcgtccag gtctgggtgc    660

gaagccaggc ccctgggcgg aggtgagggg tggtctgagg agtgatgtgg agttaaggcg    720

ccatcctcac cggtgactgg tgcggcacct agcatgtttg acaggcgggg actgcgaggc    780

acgctgctcg ggtgttgggg acaacattga ccaacgcttt attttccagg tggcagtgct    840

ccttttggac ttttctctag gtttggcgct aaactcttct tgtgagctca ctccacccct    900

tcttcctccc tttaacttat ccattcactt aaaacattac ctggtcatct ggtaagcccg    960

ggacagtaag ccgagtggct gttggagtcg gtattgttgg taatggtgga ggaagagagg   1020

ccttcccgct gaggctgggg tggggcggat cggtgttgct tgcctgcaga gagggtgggg   1080

agtgaatgtg caccccttggg tggcctgca gccatccagc tgaaagttac aaaaatgctt   1140

catggaccgt ggtttgttac tatagtgttc ctcatggcga gcagatggaa ccgggagaca   1200

tggagtccct ggccagtgtg agtcctagca ttgcaggagg ggagaccctg gaggagagag   1260

cccgcctcaa ttgatgcctg cagattgaat ttccagaggc ttaggaggag gaagttctcc   1320

aatgttctgt ttccaggcct tgctcaggaa gccctgtatt caggaggcta ccatttaaag   1380

tttgcagatg agcttatggg gggcaatctt aaaaagtcca cagcagatgc atccggctcg   1440

aggggccatc agctttgaat aaatgcttgt tccagagccc atgaatgcca gcaggcaccc   1500

ctcctttcct ggggtaaagg ttttcagatg ctgcatcttc taaattgagc ctccggtcat   1560

actagttttg tgcttggaac cttgcttcaa gaagatccct aagctgtaga acattttaac   1620

gttgatgcca caacgcagat tgatgccttg tagatggagc ttgcagatgg agccccgtga   1680

cctctcacct acccacctgt ttgcctgcct tcttgtgcgt ttctcggaga agttcttagc   1740

ctgatgaaat aacttggggc gttgaagagc tgtttaattt taaatgcctt agactgggga   1800

tatattagag gaagcagatt gtcaaattaa gggtgtcatt gtgttgtgct aaacgctggg   1860

agggtacaag ttggtcattc ctaaatctgt gtgtgagaaa tggcaggtct agtttgggca   1920

ttgtgattgc attgcagatt actaggagaa gggaatggtg ggtacaccgg tagtgctctt   1980

ttgttcttgc ttcgtttttt taaacttgaa ctttacttcg ttagatttca taatactttc   2040

ttggcattct agtaagagga ccctgaggtg ggagttgtgg gggacgggga gaaggggaca   2100

gcttggcacc ggtcccgtgg gcgttgcagt gtgggggatg gggtatgca gcttggcact   2160

ggtactggga gggatgaggg tgaagaaggg gagagggttg gttagagata cagtgtgggt   2220
```

```
ggtgggggtg gtaggaaatg caggttgaag ggaattctct ggggctttgg ggaatttagt   2280
gcgtgggtga gccaagaaaa tactaattaa taatagtaag ttgttagtgt tggttaagtt   2340
gttgcttgga agtgagaagt tgcttagaaa ctttccaaag tgcttagaac tttaagtgca   2400
aacagacaaa ctaacaaaca aaaattgttt tgctttgcta caaggtgggg aagactgaag   2460
aagtgttaac tgaaaacagg tgacacagag tcaccagttt tccgagaacc aaagggaggg   2520
gtgtgtgatg ccatctcaca ggcaggggaa atgtctttac cagcttcctc ctggtggcca   2580
agacagcctg tttcagaggg ttgttttgtt tggggtgtgg gtgttatcaa gtgaattagt   2640
cacttgaaag atgggcgtca gacttgcata cgcagcagat cagcatcctt cgctgcccct   2700
tagcaactta ggtggttgat ttgaaactgt gaaggtgtga ttttttcagg agctggaagt   2760
cttagaaaag ccttgtaaat gcctatattg tgggctttta acgtatttaa gggaccactt   2820
aagacgagat tagatgggct cttctggatt tgttcctcat ttgtcacagg tgtcttgtga   2880
ttgaaaatca tgagcgaagt gaaattgcat tgaatttcaa gggaatttag tatgtaaatc   2940
gtgccttaga aacacatctg ttgtcttttc tgtgtttggt cgatattaat aatggcaaaa   3000
tttttgccta tctagtatct tcaaattgta gtctttgtaa caaccaaata accttttgtg   3060
gtcactgtaa aattaatatt tggtagacag aatccatgta cctttgctaa ggttagaatg   3120
aataatttat tgtattttta atttgaatgt ttgtgctttt taaatgagcc aagactagag   3180
gggaaactat cacctaaaat cagtttggaa aacaagacct aaaaagggaa ggggatgggg   3240
attgtgggga gagagtgggc gaggtgcctt tactacatgt gtgatctgaa aaccctgctt   3300
ggttctgagc tgcgtctatt gaattggtaa agtaatacca atggcttttt atcatttcct   3360
tcttcccttt aagtttcact tgaaatttta aaaatcatgg ttatttttat cgttgggatc   3420
tttctgtctt ctgggttcca ttttttaaat gtttaaaaat atgttgacat ggtagttcag   3480
ttcttaacca atgacttggg gatgatgcaa acaattactg tcgttgggat ttagagtgta   3540
ttagtcacgc atgtatgggg aagtagtctc gggtatgctg ttgtgaaatt gaaactgtaa   3600
aagtagatgg ttgaaagtac tggtatgttg ctctgtatgg taagaactaa ttctgttacg   3660
tcatgtacat aattactaat cacttttctt cccctttaca gcacaaataa agtttgagtt   3720
ctaaactcat tagaattgtt gtattgctat gttacatttc tcgaccccta tcacattgcc   3780
ttcataacga ctttggatgt atcttcatat tgtagattta ggtctagatt tgctagctcc   3840
aagtaattaa ggccatgtag gagagcatgg taaccacaga tagaactggt attatcccaa   3900
gtggtctgca gactgctgag tggggatggg atctgctctc tgttgagagt tggtaatcat   3960
tggtttgaaa tgtgatgaaa ccactcaagc caatgaaggt gggtgtgtag gtggggagta   4020
ctttgccata atattttaaa acattacctg gttagagttc taagtggtac ttatttttgt   4080
ttggttaggg gaaagcctga ataaaaacag aaatggacac ataatatgca tattccatag   4140
tctttgggag gctggaatgt gcctgggatt tgggtctaag tgtatgcgta attcttacct   4200
cactaaagaa tttgccttgt ttttttcctt ttggtgagtg actaaaacgt ctgggcttcc   4260
ctgtgtgcgt gctacagtaa gcaagcagag gctgtgcaaa ggtgtgagca ggatcacgtg   4320
gaatctggag gatacatctt ggcttgcaaa ctgcctctgt ctcctgggtg ggactgttct   4380
gtccttgcac tgctgttctg tgttacctct tggggtgtaa ggttttgctt acaggagaca   4440
aactttgggc gtagaatgga agccactgcc agcctctgtg ctgagaagga aggtgcttgt   4500
ttcaaaggga gcagcaaggg aggcttgttc tactcacctg ggcctgtttg cctgagaagg   4560
ggagataagg gctgaactgg gactagccag ggggaccaac acaaatggtg ggggatcatg   4620
```

-continued

```
acctgaagga ttctttcctt cccatgagct gcagggctgg ttgccgtcct tgcaactgtg   4680
tcttatttgc ctgtgccgtt atatcttggt gacccctcca cgtgtacact actgacaaac   4740
gggtggagtg ctggggagaa gtcactgtgc cgcccaccta gtaaaccttc tgtctgtgct   4800
catggcatct ccaagatggg gcactgctgt gtgcagaatc cagggtcctc tttctgcttg   4860
caactccttt ccctggatgc cccagaaaca atccaggcct cctttcctat cttacccctt   4920
tgctttgctt tttaccccag cacctctata accgccttct cttcttttca gaactccttg   4980
tttctcgtcc tgttttttat gattacaaaa ctcttgcttc caccctggaa gataactgct   5040
atagatgcct gtatgtaaat ggtgctgtct ccagcaactg gcatgctgaa gaagaattga   5100
ttcacggggt ataaatgttg ggattggaa gtggggatga aatggcactt gttgatacag    5160
gagcagagag gtgaggccga ctgctgaaga cagctcgcca ccctccttgc ctccactcca   5220
atccaggggc tggggccaca ttctttgcct tcatttatcc tcagatcagg tgagatcgac   5280
aggaggtgtt gatggcagtg ccagcaatta ttgctaatcc gtttgcatcc ttatgcatag   5340
atctgaattc agactttgtg aatttccaga ggtgtgggta atataataga attcagtgag   5400
tgggcatggc tgatcttgtg caaattaaaa gttatggggc ataagaatag caaaagttga   5460
acttctttta aaaaggaaag taccctgaga gccagtattg gttgaggctc ttcagtatgc   5520
ccaggttggc agcactgaga accgcaggaa cggcctgttg ttacaaaaag gagattgact   5580
cagctgccct tggtgcatct gactgactat gactgctgag agattccaag gacccttaat   5640
gccagggcta acctctccat gtgcagtgag acctctggag gaagtgtcat cctctggctt   5700
tgtgtggtac tcattatggt gcagtgcggg catgaaatga agacacccaa ataggcttac   5760
agatacgata tgttttaaat gttcgtattt aacaaaaaca tactgacact gtttggaaat   5820
ggcaacagga agatagcaaa atgaatacta acattacgaa aagatgaaca ggtacatgtt   5880
ccaaggcagg tggctgtgaa cttcctctga gtgaaggcat cccctccagc acctttcagc   5940
ctgctagtta ggacgacccg ccgccaccct ccaggacctc cagccctgca ctgcctttcc   6000
tctcttttaa ataattcttc attgagttct aatatgtaaa aaaaaaaagt ttactgtaaa   6060
gtttgcaaat aaggaaattt tttttaaaag tcctcagtaa tcttaccagt aacaattgtt   6120
atgggcacat ttgcttttgg aagatttctt ttgtatgcat gggataagta catttttaaa   6180
caaaaatggg attatgccat aaattctatt ttgtgacttt aatatatagt gaacaccttt   6240
tttaatgatg acaggatgtt cccttgcatg gctgtatcaa tttaaacaat cttgtttcaa   6300
tgggcataca gggtattttc tagttttttt ttcctcttag aaaataatac ttgcgatgac   6360
tttccttgta gctcagactt tttcacgtct gttgttatct ctttgggaat gctgaataca   6420
tacatttcga gaaggaaatg actgttaaac tcttaagact tcaggttcat attgctaaac   6480
tgcccagcag ggagggattt tttcaattag tgttctcact ggtgaggcaa acctgatgcc   6540
ttcccctctt cctcagaacc ggctttatca cattgaaaac ctttgctcct ccgacggatc   6600
gagtctgctt tccctctgga tgtgagcatt gctttgtctg ctggtgactg aacatctcta   6660
ccttgtgtca attggccatt tgtggtgtgt gtgtgtgtgc gtgtgtgtgt gtgtgtgtgt   6720
gtatgatttt ctaattccta gtcatttttc tattgattgt tttgcaaaag ccatttacat   6780
cttaaggata ttgataatct tttgttatat ttgatgcaaa tattttttttc cagtttatag  6840
gttgcctttt aattttgtgt ttcaggtaga taaaagttaa acgattttct taggttagtt   6900
tatcactgtg gtttctgaac ttgttatgtg tagatctttt ccaccccaag agtacataaa   6960
```

```
tattaatcca tactttctta tggaacttgt atggtttcgt tttttacatt taaaccttct   7020
tccccgtggt gtgtgttgtg gaatctgtgt ttgtgtgagg aggggcatgg tgctctcaga   7080
acccacctcc tgtggccaga gagccctgtc ctgtgagggt ggttgtcaca gtggcagggt   7140
tcaattcaga agaccttgag ggcaggctga tgtttcctga atgggcccct ggttgttgct   7200
tgtccctgac tctccatttc cccatctgag tggatttgga cctaataggg cactggagct   7260
ggttcgaatc ctgactggac tacttggcaa ctttatgtct gggagcaagt tacttaacct   7320
ccccaagcct gtgtctgtga aatgcgggta aatgaatgta gatgtttggc agcagctact   7380
ccttgttgag ctctcacagt gaactctcct gcctctgccc tccttccccg cctcccctgg   7440
tgcctagcgt caggtctagc cacttcctcc tgggcccctc tcccttttct gtggctggct   7500
gcctgcccgc ctggcgctgg acctttcatg taacgggaat cagcatgtat attctggtct   7560
ggtctgtttc tacacttaat tttgtttcca gtagtatttc cctgtaccgg cagagttcac   7620
aaacacattt gaagaggctt tttctcagga ttcttaacct tcccaaagga agtcccatgg   7680
atgggtttct agaagtctat aaatgctctg aaattgtatt tttctgtgga aagcataact   7740
ttcatctgct tgttcgtgct caaaaaagat catgaatgaa tgattgcatg attttatgcc   7800
attgtgctta tactaaagga tatgtagccc atctcttgag ctgttaaact gttttgacta   7860
ctttaaatcg tgcagctgtg agcatctctg taaatttagt gtacacatgt atcccctgga   7920
gtggcattgc ctcggcagtg agcacttatg gttttataac tctcttcaca gactcaaatg   7980
actccagaaa gctacacttc ctgttgtgag tatatgatat ccatttccct acatagccac   8040
taacatcagg tttttacaat tttatttatt tcttgctact ttaagaaatt tttgtggtga   8100
aatacatata atagaagttg actatctgaa tcatttttaa gtatacattc agtagtgtta   8160
agtatgtcgc cattgttgta caaccaatct ccagaacttt ttcatcttgc aaaacaaact   8220
ctgtacccat taaataacat taaacattcc attccctcca gcctcagcaa ccccattcta   8280
ctttctgttt ctgtgagttt gactattcca agcacttcat atcagttaaa tcatgaagta   8340
tttgtctgtc tgtgactggc ttatttctct gagcacagtg tcctcgagat gcgtctatgt   8400
tgtagcatat gtcagaattt ccttcctttt taaaagatcc aaataatatt cttattttat   8460
atcttttttt tatccattca tccattagtg gacacttggg ttgcttttgg ctattgtaaa   8520
taatggtgct atgtacaaat atctatatta ttgtatttac aagtataatg ctgtaatgta   8580
cacacatctt tttgagatcc taccttcagt tcttttgagt atatagccag aagtggtatt   8640
actaaatctt acgatatttc tatttttaat ttattgagga accactgtag tttttcatag   8700
caactgcacc attttacgtt ctcaccaaga gtgcacaagg gttccgaggt tcccacatcc   8760
tccccaacac ttgttatttt ctgctttttt tagattgcag ccatcatagt gggtgtgagg   8820
tgacatttca ttgtggtttt gatttgcatt tccctaatga ggagtgatgc tgagcatctt   8880
ttcatatgct tactggtcat ttgtatgttg tctttggaaa aatgtctatt caagtccttt   8940
gactatttta aaaattgggt tattagagtt atcgttgttg ttgacttgta ggagtttctt   9000
tctatattct ggatattaat cccctatcag atatatgatt tgcaaatatc ttctcttatt   9060
ccataaggtt actttttcac tttgttgatt gtgttctttg atgtatagaa gtttttagtt   9120
ttgaaatagt ctaatttatc tgtttttact tttgtggtct gtgcttttgg tgtcatatcc   9180
aagaaatcct tgccaaatcc aacgttataa ggtactttta aggtatttta gttgtcttag   9240
tctatatttc tgtactcacc tttctttatc cactcatcag ttgatgggca tgtaggttgg   9300
ttccatatct ttgcaattct gaattgtgct atgatcaggt gtctttttag tataatgatt   9360
```

-continued

```
tactctcctt tgggtagata cccagtagtg ggattgctgg atcgaatggt ttttataatt   9420
ttctatttta ccacagtttc tctctgcatt tttcctcttt gaccactaac catgtgaaat   9480
tctcatattg acctttataa tgatcatgaa ctcttagtat cattgggaag gccacatttg   9540
ccacttatga ttgtaaacct tatcctccat ttttcctgtt attgttggtg caaaaagcac   9600
ctattatacc aggactttaa aaatcagtct gataagtctt tgataagtct aataataata   9660
actgataagt ccattgaatt tgcttctgat tactttttct ttagtagcta aacatgtatg   9720
tactcctatg attacaatga acactcctct ccatttaaat taattattta cattgatgaa   9780
atagcaaaat gttaatgact aaatactgtc ttggtttttt cgttccaggt cagtcaatat   9840
taacttctta taattttctt tttttcttt atgtgtgtgt gtgtgtgtat ttttttttt   9900
ttaatttcaa tggcttttgg ggtacaaatg gcttttggtc atatagatga attctacagt   9960
agtgaagtct gagattttac tgcaccggtc acctgagtag tgtacattgt acccaatatg  10020
tggtttttta taccttgccc ccctcttacc ctccccactt tgagtctcta gtgtccatta  10080
tgtcactctg tataccttttt tgtacccata agttagctct cacttataag tgagaacaca  10140
cagtatttgg ttttccattc ctgagttgct tcacttagaa taatatcctc cagctccatc  10200
caaaattgct gcaaaaaaaa aaaaaaccac aaacattatt ttgttctttt ttattgctaa  10260
gtcatattcc atggtgtaga gataccacat tttatttatc cactcactgg ttgatgggtt  10320
ggttccacat ctttgcaatt gtgacttgta ctgccatcaa gtgtctttct ggtataatga  10380
cttcttttcc tttgggtaga tacccaggag tgggattgct agatcaaatg gttcttaaca  10440
ttttctctct ggatctattt ctggaaattt taggctccag tttttgttgt tgttgttaat  10500
aaaatgcaat ggaatgtaat gatcatcact tttcattatg ctttaaaatc tggtaaatgg  10560
aggctagaac actcctgtaa ggcaagaata ttctctctgt tggaactcaa atacacagaa  10620
ctgggtaaat ctcaatctta atctttgatt caggacacaa catggctctc ttttacttgc  10680
tttctttaat tgttttttaa taatgtggta agcatttctg aatctcctat ccaatacaaa  10740
aactaggaca atacagacag taactcctat ggttacaatg aacactcctc tccacttaaa  10800
ttaattattt acactgatga aattgaaata gcaaaatttt aatgactaaa tactgtcttt  10860
gatttttgt tccaggtctg tcaatattaa cttcttataa ttttcttttt ttttctttat  10920
gtgtgtgtgt gtgtgtgtat atatatatat ttaatttcaa tggcttttgg ggtacaaatg  10980
gcttttggtc atatatatga gttctacagt agtgaagtct gagattttac tacaccttcc  11040
acttatgtgg tcccacacca cccgcctccc ctgccgcctc ctgccacccc ctaggccaag  11100
gtaataatca tcctgaatcc tgggtttatc tctcacttgc tttcttttca tataattttg  11160
caaaagaatc tgatctaaat gtgtttttca gagtatatat ttatatttta gctgttctta  11220
gagaaaattt attattttgc atgtaatctt atggaacatt ctcatttaat accatggtaa  11280
gattcagccc ttgcccaggg gatagttcat ttagtttgtt tactggatag agctcatcat  11340
gtgactatac ctcagttagt ttatcagttc tcccatccat ggtgactagg ttgcctctca  11400
gcctctcaac aacactgttt ctcagtgtcc ttgtagaagt gatatgtggg tgttttctcc  11460
ttacacagag ttgaaaggtg acgacaacaa cgttggcact accaatcccc caccctccag  11520
aggggtaacc agtgttacca gtttgctgtg tttcctgcta cacctcgcct tattcacttc  11580
catttgtatc tgaaaaacgt gttgcatggt ttcttttcta tagaagtggt aaaatgctat  11640
tgtgtcctgt acattattga ttactttttt tcatttaaca gtagggagat gcctgggagt  11700
```

-continued

```
acacagagaa ctgccctcat tgttttcaac ttctgcactg tatgtctgtg agtttagcca  11760
ttctgctgtt aatggaaatt tacagtattc taatcttttg atattacaaa cagttctgtg  11820
cgatcatcgt catacacaac cccttgtgca caatgcatga gtgtttctca gggtaggtac  11880
caagaagtga aattcctggg tcatagggcg tgagtccgac atttttctcc attctgccct  11940
gttgccctcc agagtgggtg tccagctttg catacctaag tatgagagta tctgttgttc  12000
atatcctcta cgacgctcca tatatgaaac ttaagtttct gctagttgcc atctttgatc  12060
tatcatgtat gcagtgacct actaagactg taattggtac agtagattct tgtcatctgt  12120
gtgtgaattt agcattcatg ggcttaatgc tgacaaggcc cccagggtcc aagacatata  12180
atcatgtata attttgtcaa ggtataattt tttaaattgc ttttgtcatg tgtctgctgg  12240
tgatgcccaa cccagtgctc tgcacccagg tcacactgtg gctttgtcct ctgcttatgc  12300
ctgcattgca gcaactgtcc tgaagagacc aaaattatgc agatttaggt aagtccatgg  12360
ctaatgttat tatattatgt gctattgtaa tggatggggc tgtggagtgt atgaatttat  12420
aaatcactgg tcttgtaatt aaaattcaaa cactatagaa aaaggccatg tagaagataa  12480
aagttcctct ataatcccgg acccctaaga taactactaa tgacaacttc atttatattc  12540
cttcagacat tttctggctg tggatgtact aaaatgtatc ctattattct ctgccctaaa  12600
atggaatcat acaaggtgta ctgttatttt tatggctcta taacatgtca tattgtacgt  12660
gttggtatgg tcattttaac catttttcta gtgatggctt tgaggttatt tgcagtttcc  12720
tagccatctc aaagtgtgct gcggggatct cttttgcatc cctctgggtg cagagctgag  12780
gcacccagag gcagtgtcca gaggaggcag catctgtagg tgtcttcacc tgctctggct  12840
cttggcacat ctggttggtg acactgtttt gtgagatggg ttgaaagcac gtgctgccaa  12900
aatagaataa tgttggtcct ctcctcatgt gccgtggaac tggggtaaaa ctgcgtagtg  12960
gctgcagctg cctgtccata ccggaatcga gtataacacg gtgcctggct tagcacaaaa  13020
cagtagtggg tcctgcaggc cccagagtct aattcctggt attctttccc ctacacagat  13080
taaataaacc aaaaacaaac tattctagga aagcgtctgt gacatttgta aaaagtggta  13140
tttaatgatc ttttattcac ttgtctgttt agtttgttga aatcttaagt ggcatcctgg  13200
tctgggaagg agtgctgtct gcgcctgccc tccgctgggc acagcgtggc tgcttcaggg  13260
gctaagcaca cactttctgt cttctaaagg gccgccacat gccaggagct caggtgtgag  13320
cccggctctg gctcttacct catagggtca ctcatagggg cacagggagc agaacattgt  13380
acacagcgag gcaccacccg gcttggcatc tgcctcggtg gacttactac ctctagaagg  13440
aaatacctga gttcctctgg cctcagctcc tagagtgact ggtgtgctgt ccctgttact  13500
cttctgtcaa ggtgacaact gtgtgaccca tcatctgtgt gtcaaagcaa ggccctgcct  13560
gggcctctgc tcctgtgctg accccaaagg caaatgcttt gctagtttcc ttccagttaa  13620
tttcacctat gaatagatgt gtgaaaactg ttcaaagcca tacctgcaca tgtttgaact  13680
tcaaaccctg tgggtgattc agtggcatct ttctctaacc cccagcctcc cttcccacag  13740
aggccaccgt catggccagt tgctgcagtt tctttccaga gaacctgtgt atgtgtaaag  13800
ctgtacaggc gtgggtacac cacacagcct gtcttgcact gtggactgtt gagttactag  13860
tacatctagg taagcaccgc atatctgtat tcatgtctgc cttggtcttt tcaacatctg  13920
tgtggtagcc gtgtttgaat tacccattcc ctttttgggg aaccattaag ttgtttcagc  13980
aatttttact gtagataagg ctataccgca tatctgtgta catgggtttt tatgtacatg  14040
ggcaagtata tctgtgagag aaaagtttcc tcaggaggaa ttctgggcac agcatgtgta  14100
```

-continued

```
aatttctaaa tatgatggac acccccagct tccacctcaa ggaggttggt cccattgaca  14160
tttccccaca ccttcaccca ggctgtgccc ttaaacttgg ttatttgtca atgtgagaag  14220
tggaaaatag tatttaattg tagtttggat ttgtatttct attgggttgt atacttactg  14280
attaataata agagctcttt acatattaag gaaattaacc cttttcaaat acattcctat  14340
ttctcactaa tctttaagtt ttattgtaat attttgctct ttagtttata tatatatgta  14400
tatatatata tatgtatata tatatatata catatatata tacatatata tatactaatt  14460
ttcttttatg gttcctggat tttgtgagta gtttgaaaag gctaatccag ctgaagattt  14520
tgttgttgtt gttaaacccc atgttttctc ctaactcttt ttatttttat tttggaggac  14580
tctatctaga cttaatttta gcataacaag tgacagggtt agttagcctg ttgtccttac  14640
accattttct ggctaataca gctattaact attgatctgt ctattcacgt gccagttcct  14700
aatggtttta catagtgtaa tctgcacttc aaaatagcga agggaagccc tacctcatta  14760
ttctactttt ccagaattct cctggctatt ccaggctgca tgtttacctt aaccttccct  14820
gtgatgtctt catgccgttg tcttcttatg caagaataag gtacgtcttt ccatccactc  14880
acgtctattt aatttgactt tgcattacac agaaagctgg tcttggtctg tctacctcgg  14940
catctagttg tcctcactgc cccctagccg accccacccc atctgactga ctaccccatc  15000
acagagtact tttatttacg ttttgctctg cctaatggtt acttgatact gtcacgccga  15060
cagtgtccag ttcagtggtc tttgcagttg aaatgctccc gtacacactg tcttgttaaa  15120
aatgccagta agttcataca aacccagctt gcacccaagg tcacattcag agagcgtagg  15180
gctgggatgg gttgttttcc aagcttctgc cactgtgtgg ctagctcttc ccactgggaa  15240
gttctgtgta cccggaatgt cggagtggag tcctgttcta gtgtccagca cctgaccctg  15300
tgcccaaccc ctcaacagcc tattcctgct gtccacagcc tgctggaact ttttacaaaa  15360
tatgttgcca tgctggaccc tgggcactgg acataagccc cctggcagcc tttttcatgt  15420
cacccaaagg ggtaattgtc ctactggtgg tctgtaagat gagttagggt gacttgctaa  15480
tagacattgt aaatcttaat atttatgtat gtattttatt attaccggtt ttccatttat  15540
gatggtaata ttgtttcttc taagaatatt tatttttcct tctaaatatt gagataaaat  15600
tcatgctttt gaaatgttct attcagtggc ttttagtata tttgctatgt tgtgcaacca  15660
tcgacactat ccatttctag aactttttcg tcatcccaaa cagacgctct gtattcataa  15720
aaaaataact tcctacctgt ctctccccct agtctttggt aacctttgtt atactggtaa  15780
actttgttgt gctctctgtc tgtgtgaatt tgcctattct aggggcctca tataagtgta  15840
atcatacagt atttgtcttt ttgggtctgt ctgatttcac ttagcgggtt ttcagggttc  15900
attcatgttg cagcatataa cagtactgcg ttcctttttc tggctgaata atattccact  15960
gtatggatag accccatttt gtttattcac acatcatttg gacatttgga ttatttctgg  16020
tttttggcta ttatgaacaa tggtgctatg aacagttgcg tacaagtttt tgtgtgaaca  16080
tatgttttca attctctcat tatataccta ggagtagaat tactgggtca tatggtaact  16140
gtatattttt gaggaactgc caaactattt tcccacgtcc atgcaccatt tcacattccc  16200
accagtaagt aagagggttc caatttctgc gcattcttgc caacactagt tattatctga  16260
ctttctggtt ataatcattc taatgagtgt gaagtagcct ctggtgtcat ttggatttgc  16320
atttctctga tgagtgatgc tatcaagcac ctttgctggt gctgttggcc atatgtgtat  16380
gttccctgga gaagtgtctg tgctgagcct tggcccactt tttaattagg cgtttgtctt  16440
```

```
tttattactg agttgtaaga gttctttata tattctggat tctagaccct tatcagatac  16500
atggtttgca aatattttct cccattctgt gggttgtgtt ttcactttat cgataatgtc  16560
cttagacata taataaattt gtattttaaa agtgacttga tttggctgtg caaggtggct  16620
cacgcttgta atcccagcac tttgggagac tgaggtgggt ggatcatatg aggaggctag  16680
gagttcgagg tcagcctggc cagcatagcg aaaacttgtc tctactaaaa atacaaaaat  16740
tagtcaggca tggtggtgca cgtctgtaat accagcttct caggaggctg aggcacgagg  16800
atcacttgaa cccaggagga ggaggttgca gtgagctgag atcatgccag ggcaacagaa  16860
tgagactttg tttaaaaaaa aaaaaaagtg acttgattta agggaaaaaa tgactggcta  16920
tattcagtca gatatggcaa aaagtctcaa ggtgttaatg tgaatgatta aggtcttggg  16980
gggggtgtcc cctatcagac tacaggtgtt tagaggcaca gaaaaaggtg cagttgggtt  17040
cttaatgtga aatgatgaga agcacaactc cagtgtgtct ctttgtgtag aatgtcagca  17100
gacacccccct gctagatgtg ctggatcatg ggaaagcatt tccatttgtt actagattgt  17160
tcagaagttt taatttatga tgggtgtggt ggctcatgcc tgtagtccca gcactgtggg  17220
aggctgaggc aggaggatca tctgaggcca agagttcaag atcagcctgg gcaacatagt  17280
gataccctat ctcttaaaaa agaagaagtt tttaaatttg aaataataat aggtactgga  17340
tttatgcaaa tgtcttttct gcgtcttttg agatgagtat caggtttttt tttttccttt  17400
tatcatctga tgatgaactt aatgtttcca tttgtattaa tggaatacta agtccctctg  17460
tgatttctga accaagctat tcctaggcct gagttttatt ttgttgacac agaaataaat  17520
tagaaggcca agcgtggtgg catgtgcctg tagtcctagt tgctgaggta agaggattgc  17580
ttgagcccag gagttcaagg ctgcagcaag ctttgattgc gccactgcac tccagccttg  17640
gcgacagact aagacgctgt ctcaaaaaaa aacaaaaacg acaaaaaaaa aacaaaacag  17700
aaaaaataaa ctaaggcaat gacagtccct ggcaaatgct gggagggagg cagcagtggt  17760
cagggaaggt aaccctgaag caggacttgt aaagcaaata agattgggag gccaaggtgg  17820
gtggatcacg aggtcaggag ttcgagacca gcctggccaa catagtgaaa ccccgtcttt  17880
actaaaaata caaaaaaatt agccaggtgt ggtggtgggt gcctgtagtc ccagctactt  17940
gggaggctga ggcaggagaa tctcgaaccc aggaggcgga ggttacagtc agctgagacc  18000
gcaccattgc actccagcct gggtgacaga gcaagattcc gtctcaaaaa aaaaaaaaaa  18060
aaaaaaacca agaagaaaag gaatgaatta gaacttcttc tgcttggact taagggcatc  18120
atcaggcagg ttttgggtag gatagcaggg gaggcagaga catagtcggg gtcagtggtc  18180
atgagtgtgg ctttgagccc aaaaacttgg tttctgttcc ctactttgcc actcagtagt  18240
gcatgacttt ggccaaattt cttaaattca tgaagcaagt ttccgggtga atgaaatggg  18300
gataaaaata gtgttcaaac ctatccgttg gtttgtgtga aactgaaatg aatagtatcg  18360
tgcaggtact tgtgagcaag gggagctgct gtttcctgtc cctttatgat gggaaatatc  18420
tagacaagtt cccaaccctc tgcactgcag gctgcatggc acggagggtc ttgtaacacc  18480
agctggggct ggccttcttt taggagcttc agtggttctg aaaactttta tttgtttgtt  18540
tgttttagta gatgtggggt ctttctgtgt tgcccggact ggtctcaaac ttctggactc  18600
aagtgatcct cccccgctca acctcccaaa gtgttgggat tacaggtgtg agccactgtg  18660
cccagccttg aaaacttttt caggttcttc cagggttact gggctattaa atatttctat  18720
ttcattataa gtcagttttt caaagttata ttatcttaat tacctttttt atatgtatta  18780
gtgtagagta gcattttata ttttgatatc ctccttatgc atagtttttc actttttatt  18840
```

```
cctagttttt cgtttttaat aagactttca agaaatttat tttattggcc ttttgaaaaa  18900
agcagcttta gataaagtaa gcagttctgc tttcatttta taatttattt ctacttttgt  18960
ttcattaatc ttttcctccg gcatgccttg gattttgttg tgttactctt tttctagagg  19020
ctcgcattgt gtgtctggtt cacttatgat cacgcttgcc tacttttaag aatggaagag  19080
gggaggtgga gggtggctgc acagtcgagg gtgtgaggca gtcttgctct agccccacca  19140
tgccctcagc ccgctgtggc cacgctggtt cctcaattgc tggggcgtgc agtgtctgta  19200
agggaggcta ctgatgccat ccgaggaaga tgtaaggttt cgtgtgggca gcgagagcct  19260
agcaggcatg tggggtgccc agcaaagggt aacagtggac agttgttgcc tcattccaca  19320
gagttttgat tttttttttt tttttaatgg tcactccatc aacatccccc atggccagag  19380
cctgagctgg tccccagaga cacaggcatt cagctgacag cctcgccttc acgctgctgc  19440
tgttctcatg gggggacaggc ctcaggtggc aatgcacaaa tcattagtta agggcagttg  19500
tgacagttac caaggagtgt agtcccccgc cccccgccca gtgaaaacag ccctaaccag  19560
gggtggggac ctttgggctc tgacccgaag ggtaggagaa gctggaagga cagcattcct  19620
gtctgcgaag gcaggagcaa agctgccagg ctatgaagga aatggctgga gcctgaagtc  19680
atgcaagctg gggctggcag ggacagggcc aacttccagg cctgggggcc accatgagga  19740
ttcaggacgt gacccccagg gcacatgaag gccttccatc tgtatttaag aaaagacttt  19800
atcagacgag tatggtggct cacgcctgaa tcttagcact ttgggaggct gaggcaggtg  19860
gatcacgagg tcaggagttc aataccagcc tggccaatat ggtaaaaccc catctctact  19920
aaaactacaa aaattagcca ggcatggtgg cgcacgcctg tagtcccagc tactcgggag  19980
gctgaggcag aagaatcact tgaacccggg aggtggaggt tacagtgagc caagatcgcg  20040
ccactacact ccagcctggg tgacagagtg agactccgtc tcaaaaaaac caaaagactt  20100
tatcttattt cctatatgtt tgtggtttca gtcctgatgt ataatttgac cctagttaga  20160
atggttatct gaggaagtgg cctgtacgat ttctgctttt ttaaatgtgt ggctcccttt  20220
cttcattgat taacgtatga ttatttttat aaatgttcca tggcagtggg aagggattct  20280
ctgtcacatt ccacatctgg atcagttcct ccccattttg ttggtcaaat ccgatctgcc  20340
atatcctgtg taatgacaag tgagttgcat tctcaccgtc actcctgggg tctctccgct  20400
tcccctgagc tggctcagca gtctgctcca tgtgttttga tgcagggtga cccattggta  20460
ttcccgacac taacgccccc gtctgtggac tgcttgctgc ttgggcttca ctgtgtctgg  20520
tgttgacagt gcagacctaa aggtgtgcac acatgtgcac acacactccg ctgtcttctt  20580
gtttgcactg gacttaaata tctatgaggg ttattttcaa ctgctgaatt tggaatgatt  20640
tttatatctt ttctgctttc tgcccatgta catgtgttta ttttacactg ttgtgattgg  20700
tagttactat gtggggacac aattacttgg gctgaaataa tccacctgtt gtggttgggg  20760
tcctctgggg cattccaggg tgagaggttg tcactgccac ctgggccatg tgggccggca  20820
ccagcatttt gtggttacga attctacagt cacaaatatc tttgggcaaa tccccttcta  20880
tacctcaagg cagcttttgg tttgcaaccc cactggccag agggaagggc cagtcacttg  20940
gctctctcac tgccctgcgc cccagatggt tctagggctg ctgttttccc ttggccctgc  21000
caacaccact gtttttactt ctgctcattg gctgagtgca gtggttcctg gaagccagtg  21060
gcacgtttcc ccgcgtagct cgcttatccc acagcacaca cccaagggtt ctgttgctaa  21120
cacgctgaat taattctttg ctcatcttac agagtgtgtt ttgactgccc ccatttctga  21180
```

```
ggccttgtaa ggccagagct ttgttgcttc atcggcaggt tgggacttag atggccgtga  21240
atgtttcctc tctgctgctg cagtaagtaa gtgcccgcac catagtgtgt ttggaggctg  21300
aagttgaagc gaggctgtga ggggagatgg acgtgtgagg agggatgatg gggcttgagc  21360
aaagtggggg agggggcaaa ggcagttggc ccaacacatt ccccacccct ttgagaggtc  21420
tgaggcctgc agacctggct cggagcccac ctggtagtcc tcagactgtg tgtgtgtgtg  21480
tgtgtgtgtg tgtgtgtgtg tgtgtgtgtg tgtgtgtgtg tgtgtaaaag agagaagttg  21540
tggagaaatg gggggctgat tctgctcaga ttcatcagga tgagtagaag gcacccagct  21600
ctcaccctgg cctgacatgt gtgtccctga gcaggttaca gtcctctctg agcctctgct  21660
tcccatctgg accctgctgg gcagggcttc tgagctcctt agcactagca ggaggggctc  21720
caggggccct ccctccatgg cagccaggac aggactctca aatgaggaca gcagagctcg  21780
tggggggctc ccacggaccc gccgtgggcc caggggaggc agagcctgag ccaacagcag  21840
tggtgctgtg gaccgtggat cctgagggtg gcctggggca agtaccggct gagggtccag  21900
gtgggctttg tgtacctttg ggtcctgggg ccctggtgac ttggactcca ggttagagtc  21960
aagtgacagg agaaaggctg gtggggccct gtgcttccga cttcatttcg agtgatggca  22020
gttcccagga aggaatccac agctgacggt ggctgacaga tcagagaatg gaaggcgagg  22080
caggcgggcg tctgcgtgac ctcaggtgct tggggcccag cagacccaga gaaccatttc  22140
cactaggcca gggtgccgga agtgtccaca ggtcttagat tccctgttca gatgaaaaga  22200
tttgtgcctt taatgataaa agtgatctgc atagagtcaa aaattcaagc catgggtata  22260
aaatgcaagt aaaatccctg ccctcaccta tcccacccta ctacacagag atgtcctctc  22320
gagtttccta gactcactct ggaaatttct gtatacacac agaagcttgt gcctctgctc  22380
gtgaaggcag agggagggag agctgaaggg ccagcacctt ctcacctgtg ggccccctca  22440
gtgctcggtc ccagagcatg caggactgtg cctcgtgttc agtttgctgg tctgacttca  22500
tgctccttgg gcaggatatg catgtgccat gctaggagac atgtggatgt gaagctgggg  22560
gacaatgtcc cctggctatg cctttacaag ggaagtaagg aaggtaggag gtgagcctgg  22620
gagggaggga gggaggcgcg gagccgccgc aggtgtttct tttactgagt gcagcccatg  22680
gccgcactca ggttttgctt ttcaccttcc catctgtgaa agagtgagca ggaaaaagca  22740
aaa                                                                22743
```

```
<210> SEQ ID NO 2
<211> LENGTH: 4833
<212> TYPE: DNA
<213> ORGANISM: Homo sapiens

<400> SEQUENCE: 2

gtgaactgtt gcaccgtgca attgcacact ataaatgtct ttccttatct gtgtgtactc     60
ttatctcact gttctatttt ttctcctcat ttatattaac tctttcttac ctttttttct    120
gaacttctag gccttctctt tccagaactg gtggaagaca aatgaaacgg ccaagatggt    180
aagaaacaag ccgcatttct ccttggggag actgataatt taaaaggttt gttgtgtcag    240
aaacattccc agcttcatca ccaacccttt ccttccacct ctgcccactg gagaccactt    300
atatcccgaa gcggacgcgg cagctgaagt caggaaacca tgcatcacat tagcaggagc    360
caactgcaga ctttaaactc cgttcaacat gtggatgcgg cagagaaatg acctgtccag    420
acaagccggg gcagctcata aactggttca tctgctccct gtgcgtcccg cgggtgcgta    480
agctctggag cagccggcgt ccaaggaccc ggagaaacct tctgctgggc actgcgtgtg    540
```

```
ccatctactt gggcttcctg gtgagccagg tggggagggc ctctctccag catggacagg    600
cggctgagaa ggggccacat cgcagccgcg acaccgccga gccatccttc cctgagatac    660
ccctggatgg taccctggcc cctccagagt cccagggcaa tgggtccact ctgcagccca    720
atgtggtgta cattacccta cgctccaagc gcagcaagcc ggccaatatc cgtggcaccg    780
tgaagcccaa gcgcaggaaa aagcatgcag tggcatcggc tgccccaggg caggaggctt    840
tggtcggacc atcccttcag ccgcaggaag cggcaaggga agctgatgct gtagcacctg    900
ggtacgctca gggagcaaac ctggttaaga ttggagagcg accctggagg ttggtgcggg    960
gtccgggagt gcgagccggg ggcccagact tcctgcagcc cagctccagg gagagcaaca   1020
ttaggatcta cagcgagagc gccccctcct ggctgagcaa agatgacatc cgaagaatgc   1080
gactcttggc ggacagcgca gtggcagggc tccggcctgt gtcctctagg agcggagccc   1140
gtttgctggt gctggagggg ggcgcacctg gcgctgtgct ccgctgtggc cctagcccct   1200
gtgggcttct caagcagccc ttggacatga gtgaggtgtt tgccttccac ctagacagga   1260
tcctggggct caacaggacc ctgccgtctg tgagcaggaa agcagagttc atccaagcag   1320
cagcagcagc gtgtctttcc atgcgcttgg cattctttat tttcccagcc tgggaggata   1380
tgagagttcc agggaaatgc tgtattggac atgcaagact cacctgggga acttatcagc   1440
agttgctgaa acagaaatgc tggcagaatg gccgagtacc caagcctgaa tcgggttgta   1500
ctgaaataca tcatcatgag tggtccaaga tggcactctt tgattttttg ttacagattt   1560
ataatcgctt agatacaaat tgctgtggat tcagacctcg caaggaagat gcctgtgtac   1620
agaatggatt gaggccaaaa tgtgatgacc aaggttctgc ggctctagca cacattatcc   1680
agcgaaagca tgacccaagg catttggttt ttatagacaa caagggtttc tttgacagga   1740
gtgaagataa cttaaacttc aaattgttag aaggcatcaa agagtttcca gcttctgcag   1800
tttctgtttt gaagagccag cacttacggc agaaacttct tcagtctctg tttcttgata   1860
aagtgtattg ggaaagtcaa ggaggtagac aaggaattga aaagcttatc gatgtaatag   1920
aacacagagc caaaattctt atcacctata tcaatgcaca cggggtcaaa gtattaccta   1980
tgaatgaatg acaaaagaat cttctggcta gggtgttaga tatatttatg catttttggt   2040
tttgttttta aatcaagcac atcaacctca agcccgttta gcaatgaggc agtgtagatg   2100
aatacgtaaa ataaatgact ttaaccaagt agctataatg ggacttagca ctgtatgcat   2160
acttaaaaag gttttgaaaa acaaactact tgagaaatat ttgtttatat ttttctctaa   2220
catcatgcta tgtgtcagtc tgaacatctg acaacagaaa tttcagttat tattctagct   2280
aagttttgaa aacatttgtc atgctgttta atagaaaact gcaaaccaga gacactgact   2340
ccattaataa accatatttt gtgccgtttt gactgttctg accaaatact aatgggaaca   2400
attcttgacg tttttctgtt gctgattgtt aacatagagc agtctctaca ctaccctgag   2460
gcaactctac attggaacac tgaggcttac agcctgcaag agcatcagag ctgaccatac   2520
atttaaacag aaatgctggt ttatttgcaa aatcaccagt atattttcta ttgtgtctat   2580
aaaaaatcag tcatttaagt acaagaatca tattttccat tcctttttag aaatttattt   2640
tgttgtccct atggaaatca ttcacatctg acaatttata tgttaaagag ttttactctc   2700
tctattttgg tccaatttgt atctagtggc tgagaaatta aataattcta aagtatgaag   2760
ttacctatct gaaaatgtac ttacagagta tcattttaaa atggatgtct ctttaaaaat   2820
tttgttactt ttaccaacaa tgtaatataa tttatgtata ttttattaat aatagtgaat   2880
```

```
tccttaaaat ttgttctatg tacttatatt taatttgatt taatggttac tgcccagata   2940
ttgagaattg gttcaaatat tgagtgtgtt tcaatatatt atctggctta tttcaacatg   3000
agtaatatga gcaaaataag ttaaaacctg cgtctgatca attttcctca tgactagaac   3060
taaaacagta aatttggaca atattaagcc tcaaataatc atctccaaac tccttctaac   3120
actttttaaa tcagattgga agacatggac aaatcaggtt catgtgttgc atctttatgt   3180
cctttgccaa tatccaagat catcacatat ggtagatatt cacatggagt ttcaaattca   3240
gaatagatta ccattacctt cctgccctta cacatcctac tccttattta aaagttctat   3300
ttgtgacttt tcatttcctg aaagtttaaa aatacaattt gagaatgttt ataatacatt   3360
ctctcctgtc ttttcacggt tacgtctgtt attgctgaaa tacaccacat tttctttgtt   3420
ctggtcaagg ttaactcaat atctgtgtga aagagaacta ctaacaacgt tacaatagag   3480
gctagatttg aaaaaaaaaa tctatagatc taattgatac aattgtagaa caaaatgtca   3540
aaataatgtt ttaagtataa gagaagatgg accaaggaga gagagatcat ttgaaaatct   3600
aattgtagct tttctaggct cacattcatg tactactttt agcaccctta tgggctgtgc   3660
tcgccccctg gacagttgag ctttggatta tcttcctctt caattttccc tctattgacc   3720
cgagtgtctc cctctgcttc tacagattta tagtactcct tggctctttt gagtctccac   3780
ttttactcac tgtctctggg atttttaaga tccttttctt ctcttataaa tcatcctctt   3840
aatgaaaatt agcctaacaa aagtttggag actggaatcc tactttgagc cactgacttg   3900
aaataactct tttggcaagt tgcctgacat cctgtcttac caaggtggca tatttgcatt   3960
tttactgctt aaaacatttt ttttttttta ccatctttat ccaaatttat catattgatg   4020
gtaggactaa caggcttttt agaagctggc tttaactttg agtctcaagc tacaatgctg   4080
ttgggcagcc tggtcttccc acgtgagggt ttaactttgt ttatttgcct ccagttattc   4140
caaaatgctt attaaatgaa agtcccagga acatgtttat tttagtcacc tttgcttttt   4200
aacaattttg ttttgtaatc aatgagtaat tcatgatgaa ttatttttga ctaatggata   4260
gccgaaggcc aggcttttaa ttctaatagg taatgttctt cttttgtctt attgaaacaa   4320
tgagaatact ctgtgcattt caaatgcact ccgattatgc tgtggtttta ttcacataag   4380
cacaatatgt gttttattta taacttcata acaaacttat aatataataa tttaccttag   4440
cagacatgca aaagcttatt cttgtgtgac ttactttctt taagctaata atataaaaat   4500
aaatatgtat cttaaaaatc tataataaaa cattagaaat taaagatatg tgctttttat   4560
tttgcagatg agttcatttg cttttgtaga tgtgttttca gagctaggta cagaggaatg   4620
tttgctacct ttagcggtga aaaaagaaag agagtcaaga attttgttgg attgtgtttg   4680
tgtgtgcata tatttgatat catcattata tttgtaatct ttggacttgt aatcatagcc   4740
tgtttattct actgtgccat taaatatact ttaccttata cataacgaat aaaataccta   4800
gaagtagatt tatttacaaa aaaaaaaaaa aaa                                4833
```

<210> SEQ ID NO 3
<211> LENGTH: 4854
<212> TYPE: DNA
<213> ORGANISM: Homo sapiens

<400> SEQUENCE: 3

```
gtttttaaaa gctttgtatc tcttaaaacc atgcagcagt cagtttccaa gttttgcttt     60
gcaatcagta gttttcaagg gagcttttaa agctgaactg aaatgtttga aatgtggaac    120
actcttgacc atgaaatatg ttctacttac atgcctcagc ctttaaaagt tctttgcatt    180
```

-continued

```
agagtcaagg attacattct tcctggagcc aagcatgggg ccagctgtaa acaagccgca    240
tttctccttg ggagactgga taatttaaaa ggtttgttgt gtcagaaaca ttcccagctt    300
catcaccaac cctttccttc cacctctgcc cactggagac cacttatatc ccgaagcgga    360
cgcggcagct gaagtcagga aaccatgcat cacattagca ggagccaact gcagacttta    420
aactccgttc aacatgtgga tgcggcagag aaatgacctg tccagacaag ccggggcagc    480
tcataaactg gttcatctgc tccctgtgcg tcccgcgggt gcgtaagctc tggagcagcc    540
ggcgtccaag gacccggaga aaccttctgc tgggcactgc gtgtgccatc tacttgggct    600
tcctggtgag ccaggtgggg agggcctctc tccagcatgg acaggcggct gagaaggggc    660
cacatcgcag ccgcgacacc gccgagccat ccttccctga gataccccctg gatggtaccc   720
tggcccctcc agagtcccag ggcaatgggt ccactctgca gcccaatgtg gtgtacatta    780
ccctacgctc caagcgcagc aagccggcca atatccgtgg caccgtgaag cccaagcgca    840
ggaaaaagca tgcagtggca tcggctgccc cagggcagga ggctttggtc ggaccatccc    900
ttcagccgca ggaagcggca agggaagctg atgctgtagc acctgggtac gctcagggag    960
caaacctggt taagattgga gagcgaccct ggaggttggt gcggggtccg ggagtgcgag   1020
ccgggggccc agacttcctg cagcccagct ccagggagag caacattagg atctacagcg   1080
agagcgcccc ctcctggctg agcaaagatg acatccgaag aatgcgactc ttggcggaca   1140
gcgcagtggc agggctccgg cctgtgtcct ctaggagcgg agcccgtttg ctggtgctgg   1200
agggggcgc acctggcgct gtgctccgct gtggccctag cccctgtggg cttctcaagc    1260
agcccttgga catgagtgag gtgtttgcct tccacctaga caggatcctg ggctcaaca    1320
ggaccctgcc gtctgtgagc aggaaagcag agttcatcca agatggccgc ccatgcccca   1380
tcattctttg ggatgcatct ttatcttcag caagtaatga cacccattct tctgttaagc   1440
tcacctgggg aacttatcag cagttgctga aacagaaatg ctggcagaat ggccgagtac   1500
ccaagcctga atcgggttgt actgaaatac atcatcatga gtggtccaag atggcactct   1560
ttgatttttt gttacagatt tataatcgct tagatacaaa ttgctgtgga ttcagacctc   1620
gcaaggaaga tgcctgtgta cagaatggat tgaggccaaa atgtgatgac caaggttctg   1680
cggctctagc acacattatc cagcgaaagc atgacccaag gcatttggtt tttatagaca   1740
acaagggttt ctttgacagg agtgaagata acttaaactt caaattgtta gaaggcatca   1800
aagagtttcc agcttctgca gtttctgttt tgaagagcca gcacttacgg cagaaacttc   1860
ttcagtctct gtttcttgat aaagtgtatt gggaaagtca aggaggtaga caaggaattg   1920
aaaagcttat cgatgtaata gaacacagag ccaaaattct tatcacctat atcaatgcac   1980
acggggtcaa agtattacct atgaatgaat gacaaaagaa tcttctggct agggtgttag   2040
atatatttat gcatttttgg ttttgttttt aaatcaagca catcaacctc aagcccgttt   2100
agcaatgagg cagtgtagat gaatacgtaa aataaatgac tttaaccaag tagctataat   2160
gggacttagc actgtatgca tacttaaaaa ggttttgaaa aacaaactac ttgagaaata   2220
tttgtttata tttttctcta acatcatgct atgtgtcagt ctgaacatct gacaacagaa   2280
atttcagtta ttattctagc taagttttga aaacatttgt catgctgttt aatagaaaac   2340
tgcaaaccag agacactgac tccattaata aaccatattt tgtgccgttt tgactgttct   2400
gaccaaatac taatgggaac aattcttgac gtttttctgt tgctgattgt taacatagag   2460
cagtctctac actaccctga ggcaactcta cattggaaca ctgaggctta cagcctgcaa   2520
```

```
gagcatcaga gctgaccata catttaaaca gaaatgctgg tttatttgca aaatcaccag   2580

tatattttct attgtgtcta taaaaaatca gtcatttaag tacaagaatc atattttcca   2640

ttccttttta gaaatttatt ttgttgtccc tatggaaatc attcacatct gacaatttat   2700

atgttaaaga gttttactct ctctattttg gtccaatttg tatctagtgg ctgagaaatt   2760

aaataattct aaagtatgaa gttacctatc tgaaaatgta cttacagagt atcattttaa   2820

aatggatgtc tctttaaaaa ttttgttact tttaccaaca atgtaatata atttatgtat   2880

attttattaa taatagtgaa ttccttaaaa tttgttctat gtacttatat ttaatttgat   2940

ttaatggtta ctgcccagat attgagaatt ggttcaaata ttgagtgtgt ttcaatatat   3000

tatctggctt atttcaacat gagtaatatg agcaaaataa gttaaaacct gcgtctgatc   3060

aattttcctc atgactagaa ctaaaacagt aaatttggac aatattaagc ctcaaataat   3120

catctccaaa ctccttctaa cactttttaa atcagattgg aagacatgga caaatcaggt   3180

tcatgtgttg catctttatg tcctttgcca atatccaaga tcatcacata tggtagatat   3240

tcacatggag tttcaaattc agaatagatt accattacct tcctgccctt acacatccta   3300

ctccttattt aaaagttcta tttgtgactt ttcatttcct gaaagtttaa aaatacaatt   3360

tgagaatgtt tataatacat tctctcctgt cttttcacgg ttacgtctgt tattgctgaa   3420

atacaccaca ttttctttgt tctggtcaag gttaactcaa tatctgtgtg aaagagaact   3480

actaacaacg ttacaataga ggctagattt gaaaaaaaaa atctatagat ctaattgata   3540

caattgtaga acaaaatgtc aaaataatgt tttaagtata agagaagatg gaccaaggag   3600

agagagatca tttgaaaatc taattgtagc ttttctaggc tcacattcat gtactacttt   3660

tagcaccctt atgggctgtg ctcgccccct ggacagttga gctttggatt atcttcctct   3720

tcaattttcc ctctattgac ccgagtgtct ccctctgctt ctacagattt atagtactcc   3780

ttggctcttt tgagtctcca cttttactca ctgtctctgg gatttttaag atccttttct   3840

tctcttataa atcatcctct taatgaaaat tagcctaaca aaagtttgga gactggaatc   3900

ctactttgag ccactgactt gaaataactc ttttggcaag ttgcctgaca tcctgtctta   3960

ccaaggtggc atatttgcat ttttactgct taaaacattt tttttttttt accatcttta   4020

tccaaattta tcatattgat ggtaggacta acaggctttt tagaagctgg ctttaacttt   4080

gagtctcaag ctacaatgct gttgggcagc ctggtcttcc cacgtgaggg tttaactttg   4140

tttatttgcc tccagttatt ccaaaatgct tattaaatga aagtcccagg aacatgttta   4200

ttttagtcac ctttgctttt taacaatttt gttttgtaat caatgagtaa ttcatgatga   4260

attattttg actaatggat agccgaaggc caggctttta attctaatag gtaatgttct   4320

tcttttgtct tattgaaaca atgagaatac tctgtgcatt tcaaatgcac tccgattatg   4380

ctgtggtttt attcacataa gcacaatatg tgttttattt ataacttcat aacaaactta   4440

taatataata atttacctta gcagacatgc aaaagcttat tcttgtgtga cttactttct   4500

ttaagctaat aatataaaaa taaatatgta tcttaaaaat ctataataaa acattagaaa   4560

ttaaagatat gtgcttttta ttttgcagat gagttcattt gcttttgtag atgtgttttc   4620

agagctaggt acagaggaat gtttgctacc tttagcggtg aaaaaagaaa gagagtcaag   4680

aattttgttg gattgtgttt gtgtgtgcat atatttgata tcatcattat atttgtaatc   4740

tttggacttg taatcatagc ctgtttattc tactgtgcca ttaaatatac tttaccttat   4800

acataacgaa taaaatacct agaagtagat ttatttacaa aaaaaaaaaa aaaa         4854
```

```
<210> SEQ ID NO 4
<211> LENGTH: 4809
<212> TYPE: DNA
<213> ORGANISM: Homo sapiens

<400> SEQUENCE: 4

gtgaactgtt gcaccgtgca attgcacact ataaatgtct ttccttatct gtgtgtactc     60

ttatctcact gttctatttt ttctcctcat ttatattaac tctttcttac cttttttttct   120

gaacttctag gccttctctt tccagaactg gtggaagaca aatgaaacgg ccaagatggt    180

aagaaacaag ccgcatttct ccttggggag actgataatt taaaaggttt gttgtgtcag    240

aaacattccc agcttcatca ccaacccttt ccttccacct ctgcccactg gagaccactt    300

atatcccgaa gcggacgcgg cagctgaagt caggaaacca tgcatcacat tagcaggagc    360

caactgcaga ctttaaactc cgttcaacat gtggatgcgg cagagaaatg acctgtccag    420

acaagccggg gcagctcata aactggttca tctgctccct gtgcgtcccg cgggtgcgta    480

agctctggag cagccggcgt ccaaggaccc ggagaaacct tctgctgggc actgcgtgtg    540

ccatctactt gggcttcctg gtgagccagg tggggagggc ctctctccag catggacagg    600

cggctgagaa ggggccacat cgcagccgcg acaccgccga gccatccttc cctgagatac    660

ccctggatgg taccctggcc cctccagagt cccagggcaa tgggtccact ctgcagccca    720

atgtggtgta cattacccta cgctccaagc gcagcaagcc ggccaatatc cgtggcaccg    780

tgaagcccaa gcgcaggaaa aagcatgcag tggcatcggc tgccccaggg caggaggctt    840

tggtcggacc atcccttcag ccgcaggaag cggcaaggga agctgatgct gtagcacctg    900

ggtacgctca gggagcaaac ctggttaaga ttggagagcg accctggagg ttggtgcggg    960

gtccgggagt gcgagccggg ggcccagact tcctgcagcc cagctccagg gagagcaaca   1020

ttaggatcta cagcgagagc gccccctcct ggctgagcaa agatgacatc cgaagaatgc   1080

gactcttggc ggacagcgca gtggcagggc tccggcctgt gtcctctagg agcggagccc   1140

gtttgctggt gctggagggg ggcgcacctg gcgctgtgct ccgctgtggc cctagcccct   1200

gtgggcttct caagcagccc ttggacatga gtgaggtgtt tgccttccac ctagacagga   1260

tcctggggct caacaggacc ctgccgtctg tgagcaggaa agcagagttc atccaagatg   1320

gccgcccatg ccccatcatt ctttgggatg catctttatc ttcagcaagt aatgacaccc   1380

attcttctgt taagctcacc tggggaactt atcagcagtt gctgaaacag aaatgctggc   1440

agaatggccg agtacccaag cctgaatcgg gttgtactga aatacatcat catgagtggt   1500

ccaagatggc actctttgat tttttgttac agatttataa tcgcttagat acaaattgct   1560

gtggattcag acctcgcaag gaagatgcct gtgtacagaa tggattgagg ccaaaatgtg   1620

atgaccaagg ttctgcggct ctagcacaca ttatccagcg aaagcatgac ccaaggcatt   1680

tggtttttat agacaacaag ggtttctttg acaggagtga agataactta aacttcaaat   1740

tgttagaagg catcaaagag tttccagctt ctgcagtttc tgttttgaag agccagcact   1800

tacggcagaa acttcttcag tctctgtttc ttgataaagt gtattgggaa agtcaaggag   1860

gtagacaagg aattgaaaag cttatcgatg taatagaaca cagagccaaa attcttatca   1920

cctatatcaa tgcacacggg gtcaaagtat tacctatgaa tgaatgacaa aagaatcttc   1980

tggctagggt gttagatata tttatgcatt tttggttttg tttttaaatc aagcacatca   2040

acctcaagcc cgtttagcaa tgaggcagtg tagatgaata cgtaaaataa atgactttaa   2100

ccaagtagct ataatgggac ttagcactgt atgcatactt aaaaaggttt tgaaaaacaa   2160
```

-continued

```
actacttgag aaatatttgt ttatattttt ctctaacatc atgctatgtg tcagtctgaa   2220
catctgacaa cagaaatttc agttattatt ctagctaagt tttgaaaaca tttgtcatgc   2280
tgtttaatag aaaactgcaa accagagaca ctgactccat taataaacca tattttgtgc   2340
cgttttgact gttctgacca aatactaatg ggaacaattc ttgacgtttt tctgttgctg   2400
attgttaaca tagagcagtc tctacactac cctgaggcaa ctctacattg gaacactgag   2460
gcttacagcc tgcaagagca tcagagctga ccatacattt aaacagaaat gctggtttat   2520
ttgcaaaatc accagtatat tttctattgt gtctataaaa aatcagtcat ttaagtacaa   2580
gaatcatatt ttccattcct ttttagaaat ttattttgtt gtccctatgg aaatcattca   2640
catctgacaa tttatatgtt aaagagtttt actctctcta ttttggtcca atttgtatct   2700
agtggctgag aaattaaata attctaaagt atgaagttac ctatctgaaa atgtacttac   2760
agagtatcat tttaaaatgg atgtctcttt aaaaatttg ttacttttac caacaatgta   2820
atataattta tgtatatttt attaataata gtgaattcct taaaatttgt tctatgtact   2880
tatatttaat ttgatttaat ggttactgcc cagatattga gaattggttc aaatattgag   2940
tgtgtttcaa tatattatct ggcttatttc aacatgagta atatgagcaa aataagttaa   3000
aacctgcgtc tgatcaattt tcctcatgac tagaactaaa acagtaaatt tggacaatat   3060
taagcctcaa ataatcatct ccaaactcct tctaacactt tttaaatcag attggaagac   3120
atggacaaat caggttcatg tgttgcatct ttatgtcctt tgccaatatc caagatcatc   3180
acatatggta gatattcaca tggagtttca aattcagaat agattaccat taccttcctg   3240
cccttacaca tcctactcct tatttaaaag ttctatttgt gacttttcat ttcctgaaag   3300
tttaaaaata caatttgaga atgtttataa tacattctct cctgtctttt cacggttacg   3360
tctgttattg ctgaaataca ccacattttc tttgttctgg tcaaggttaa ctcaatatct   3420
gtgtgaaaga gaactactaa caacgttaca atagaggcta gatttgaaaa aaaaaatcta   3480
tagatctaat tgatacaatt gtagaacaaa atgtcaaaat aatgttttaa gtataagaga   3540
agatggacca aggagagaga gatcatttga aaatctaatt gtagcttttc taggctcaca   3600
ttcatgtact acttttagca cccttatggg ctgtgctcgc cccctggaca gttgagcttt   3660
ggattatctt cctcttcaat ttccctcta ttgacccgag tgtctccctc tgcttctaca   3720
gatttatagt actccttggc tcttttgagt ctccactttt actcactgtc tctgggattt   3780
ttaagatcct tttcttctct tataaatcat cctcttaatg aaaattagcc taacaaaagt   3840
ttggagactg gaatcctact ttgagccact gacttgaaat aactcttttg gcaagttgcc   3900
tgacatcctg tcttaccaag gtggcatatt tgcattttta ctgcttaaaa cattttttt   3960
tttttaccat ctttatccaa atttatcata ttgatggtag gactaacagg ctttttagaa   4020
gctggcttta actttgagtc tcaagctaca atgctgttgg gcagcctggt cttcccacgt   4080
gagggtttaa ctttgtttat ttgcctccag ttattccaaa atgcttatta aatgaaagtc   4140
ccaggaacat gtttatttta gtcacctttg ctttttaaca attttgtttt gtaatcaatg   4200
agtaattcat gatgaattat ttttgactaa tggatagccg aaggccaggc ttttaattct   4260
aataggtaat gttcttcttt tgtcttattg aaacaatgag aatactctgt gcatttcaaa   4320
tgcactccga ttatgctgtg gttttattca cataagcaca atatgtgttt tatttataac   4380
ttcataacaa acttataata taataattta ccttagcaga catgcaaaag cttattcttg   4440
tgtgacttac tttctttaag ctaataatat aaaaataaat atgtatctta aaaatctata   4500
ataaaacatt agaaattaaa gatatgtgct ttttattttg cagatgagtt catttgcttt   4560
```

```
tgtagatgtg ttttcagagc taggtacaga ggaatgtttg ctacctttag cggtgaaaaa   4620

agaaagagag tcaagaattt tgttggattg tgtttgtgtg tgcatatatt tgatatcatc   4680

attatatttg taatctttgg acttgtaatc atagcctgtt tattctactg tgccattaaa   4740

tatactttac cttatacata acgaataaaa tacctagaag tagatttatt tacaaaaaaa   4800

aaaaaaaaa                                                           4809
```

```
<210> SEQ ID NO 5
<211> LENGTH: 4745
<212> TYPE: DNA
<213> ORGANISM: Homo sapiens

<400> SEQUENCE: 5

ttttctgccc ttctttgctt tggtggcttc cttgtggttc ctcagtggtg cctgcaaccc     60

ctggttcacc tccttccagg ttctggctcc ttccagccat ggctctcaga gtccttctgt    120

taacagcctt gaccttatgt catgggttca acttggacac tgaaaacgca atgaccttcc    180

aagagaacgc aaggggcttc gggcagagcg tggtccagct tcagggatcc agggtggtgg    240

ttggagcccc ccaggagata gtggctgcca accaaagggg cagcctctac cagtgcgact    300

acagcacagg ctcatgcgag cccatccgcc tgcaggtccc cgtggaggcc gtgaacatgt    360

ccctgggcct gtccctggca gccaccacca gccccccctca gctgctggcc tgtggtccca    420

ccgtgcacca gacttgcagt gagaacacgt atgtgaaagg gctctgcttc ctgtttggat    480

ccaacctacg gcagcagccc cagaagttcc cagaggccct ccgagggtgt cctcaagagg    540

atagtgacat tgccttcttg attgatggct ctggtagcat catcccacat gactttcggc    600

ggatgaagga gtttgtctca actgtgatgg agcaattaaa aaagtccaaa accttgttct    660

ctttgatgca gtactctgaa gaattccgga ttcactttac cttcaaagag ttccagaaca    720

accctaaccc aagatcactg gtgaagccaa taacgcagct gcttgggcgg acacacacgg    780

ccacgggcat ccgcaaagtg gtacgagagc tgtttaacat caccaacgga gcccgaaaga    840

atgcctttaa gatcctagtt gtcatcacgg atggagaaaa gtttggcgat cccttgggat    900

atgaggatgt catccctgag gcagacagag agggagtcat tcgctacgtc attggggtgg    960

gagatgcctt ccgcagtgag aaatcccgcc aagagcttaa taccatcgca tccaagccgc   1020

ctcgtgatca cgtgttccag gtgaataact ttgaggctct gaagaccatt cagaaccagc   1080

ttcgggagaa gatctttgcg atcgagggta ctcagacagg aagtagcagc tcctttgagc   1140

atgagatgtc tcaggaaggc ttcagcgctg ccatcacctc taatggcccc ttgctgagca   1200

ctgtggggag ctatgactgg gctggtggag tctttctata tacatcaaag gagaaaagca   1260

ccttcatcaa catgaccaga gtggattcag acatgaatga tgcttacttg ggttatgctg   1320

ccgccatcat cttacggaac cgggtgcaaa gcctggttct gggggcacct cgatatcagc   1380

acatcggcct ggtagcgatg ttcaggcaga acactggcat gtgggagtcc aacgctaatg   1440

tcaagggcac ccagatcggc gcctacttcg gggcctccct ctgctccgtg gacgtggaca   1500

gcaacggcag caccgacctg gtcctcatcg gggcccccca ttactacgag cagacccgag   1560

ggggccaggt gtccgtgtgc cccttgccca gggggcagag ggctcggtgg cagtgtgatg   1620

ctgttctcta cggggagcag ggccaaccct ggggccgctt tggggcagcc ctaacagtgc   1680

tgggggacgt aaatggggac aagctgacgg acgtggccat tggggcccca ggagaggagg   1740

acaaccgggg tgctgtttac ctgtttcacg gaacctcagg atctggcatc agcccctccc   1800
```

```
atagccagcg gatagcaggc tccaagctct ctcccaggct ccagtatttt ggtcagtcac   1860
tgagtggggg ccaggacctc acaatggatg gactggtaga cctgactgta ggagcccagg   1920
ggcacgtgct gctgctcagg tcccagccag tactgagagt caaggcaatc atggagttca   1980
atcccaggga agtggcaagg aatgtatttg agtgtaatga tcaggtggtg aaaggcaagg   2040
aagccggaga ggtcagagtc tgcctccatg tccagaagag cacacgggat cggctaagag   2100
aaggacagat ccagagtgtt gtgacttatg acctggctct ggactccggc cgcccacatt   2160
cccgcgccgt cttcaatgag acaaagaaca gcacacgcag acagacacag gtcttggggc   2220
tgacccagac ttgtgagacc ctgaaactac agttgccgaa ttgcatcgag gacccagtga   2280
gccccattgt gctgcgcctg aacttctctc tggtgggaac gccattgtct gctttcggga   2340
acctccggcc agtgctggcg gaggatgctc agagactctt cacagccttg tttccctttg   2400
agaagaattg tggcaatgac aacatctgcc aggatgacct cagcatcacc ttcagtttca   2460
tgagcctgga ctgcctcgtg gtgggtgggc cccgggagtt caacgtgaca gtgactgtga   2520
gaaatgatgg tgaggactcc tacaggacac aggtcacctt cttcttcccg cttgacctgt   2580
cctaccggaa ggtgtccacg ctccagaacc agcgctcaca gcgatcctgg cgcctggcct   2640
gtgagtctgc ctcctccacc gaagtgtctg ggccttgaa gagcaccagc tgcagcataa    2700
accaccccat cttcccggaa aactcagagg tcacctttaa tatcacgttt gatgtagact   2760
ctaaggcttc ccttggaaac aaactgctcc tcaaggccaa tgtgaccagt gagaacaaca   2820
tgcccagaac caacaaaacc gaattccaac tggagctgcc ggtgaaatat gctgtctaca   2880
tggtggtcac cagccatggg gtctccacta aatatctcaa cttcacggcc tcagagaata   2940
ccagtcgggt catgcagcat caatatcagg tcagcaacct ggggcagagg agcctcccca   3000
tcagcctggt gttcttggtg cccgtccggc tgaaccagac tgtcatatgg gaccgccccc   3060
aggtcacctt ctccgagaac ctctcgagta cgtgccacac caaggagcgc ttgccctctc   3120
actccgactt tctggctgag cttcggaagg cccccgtggt gaactgctcc atcgctgtct   3180
gccagagaat ccagtgtgac atcccgttct ttggcatcca ggaagaattc aatgctaccc   3240
tcaaaggcaa cctctcgttt gactggtaca tcaagacctc gcataaccac ctcctgatcg   3300
tgagcacagc tgagatcttg tttaacgatt ccgtgttcac cctgctgccg ggacaggggg   3360
cgtttgtgag gtcccagacg gagaccaaag tggagccgtt cgaggtcccc aaccccctgc   3420
cgctcatcgt gggcagctct gtcgggggac tgctgctcct ggccctcatc accgccgcgc   3480
tgtacaagct cggcttcttc aagcggcaat acaaggacat gatgagtgaa gggggtcccc   3540
cgggggccga accccagtag cggctccttc ccgacagagc tgcctctcgg tggccagcag   3600
gactctgccc agaccacacg tagcccccag gctgctggac acgtcggaca gcgaagtatc   3660
cccgacagga cgggcttggg cttccatttg tgtgtgtgca agtgtgtatg tgcgtgtgtg   3720
caagtgtctg tgtgcaagtg tgtgcacatg tgtgcgtgtg cgtgcatgtg cacttgcacg   3780
cccatgtgtg agtgtgtgca agtatgtgag tgtgtccaag tgtgtgtgcg tgtgtccatg   3840
tgtgtgcaag tgtgtgcatg tgtgcgagtg tgtgcatgtg tgtgctcagg ggcgtgtggc   3900
tcacgtgtgt gactcagatg tctctggcgt gtgggtaggt gacggcagcg tagcctctcc   3960
ggcagaaggg aactgcctgg gctcccttgt gcgtgggtga agccgctgct gggttttcct   4020
ccgggagagg ggacggtcaa tcctgtgggt gaagacagag ggaaacacag cagcttctct   4080
ccactgaaag aagtgggact tcccgtcgcc tgcgagcctg cggcctgctg gagcctgcgc   4140
agcttggatg gagactccat gagaagccgt gggtggaacc aggaacctcc tccacaccag   4200
```

```
cgctgatgcc caataaagat gcccactgag gaatgatgaa gcttcctttc tggattcatt   4260

tattatttca atgtgacttt aattttttgg atggataagc ttgtctatgg tacaaaaatc   4320

acaaggcatt caagtgtaca gtgaaaagtc tccctttcca gatattcaag tcacctcctt   4380

aaaggtagtc aagattgtgt tttgaggttt ccttcagaca gattccaggc gatgtgcaag   4440

tgtatgcacg tgtgcacaca caccacacat acacacacac aagctttttt acacaaatgg   4500

tagcatactt tatattggtc tgtatcttgc tttttttcac caatatttct cagacatcgg   4560

ttcatattaa gacataaatt actttttcat tcttttatac cgctgcatag tattccattg   4620

tgtgagtgta ccataatgta tttaaccagt cttcttttga tatactattt tcattctctt   4680

gttattgcat caatgctgag ttaataaatc aaatatatgt catttttgca tatatgtaag   4740

gataa                                                               4745
```

<210> SEQ ID NO 6
<211> LENGTH: 4742
<212> TYPE: DNA
<213> ORGANISM: Homo sapiens

<400> SEQUENCE: 6

```
ttttctgccc ttctttgctt tggtggcttc cttgtggttc ctcagtggtg cctgcaaccc     60

ctggttcacc tccttccagg ttctggctcc ttccagccat ggctctcaga gtccttctgt    120

taacagcctt gaccttatgt catgggttca acttggacac tgaaaacgca atgaccttcc    180

aagagaacgc aaggggcttc gggcagagcg tggtccagct tcagggatcc agggtggtgg    240

ttggagcccc ccaggagata gtggctgcca accaaagggg cagcctctac cagtgcgact    300

acagcacagg ctcatgcgag cccatccgcc tgcaggtccc cgtggaggcc gtgaacatgt    360

ccctgggcct gtccctggca gccaccacca gccccccctca gctgctggcc tgtggtccca    420

ccgtgcacca gacttgcagt gagaacacgt atgtgaaagg gctctgcttc ctgtttggat    480

ccaacctacg gcagcagccc cagaagttcc cagaggccct ccgagggtgt cctcaagagg    540

atagtgacat tgccttcttg attgatggct ctggtagcat catcccacat gactttcggc    600

ggatgaagga gtttgtctca actgtgatgg agcaattaaa aaagtccaaa accttgttct    660

ctttgatgca gtactctgaa gaattccgga ttcactttac cttcaaagag ttccagaaca    720

accctaaccc aagatcactg gtgaagccaa taacgcagct gcttgggcgg acacacacgg    780

ccacgggcat ccgcaaagtg gtacgagagc tgtttaacat caccaacgga gcccgaaaga    840

atgcctttaa gatcctagtt gtcatcacgg atggagaaaa gtttggcgat cccttgggat    900

atgaggatgt catccctgag gcagacagag agggagtcat tcgctacgtc attggggtgg    960

gagatgcctt ccgcagtgag aaatcccgcc aagagcttaa taccatcgca tccaagccgc   1020

ctcgtgatca cgtgttccag gtgaataact ttgaggctct gaagaccatt cagaaccagc   1080

ttcgggagaa gatctttgcg atcgagggta ctcagacagg aagtagcagc tcctttgagc   1140

atgagatgtc tcaggaaggc ttcagcgctg ccatcacctc taatggcccc ttgctgagca   1200

ctgtggggag ctatgactgg gctggtggag tctttctata tacatcaaag gagaaaagca   1260

ccttcatcaa catgaccaga gtggattcag acatgaatga tgcttacttg ggttatgctg   1320

ccgccatcat cttacggaac cgggtgcaaa gcctggttct gggggcacct cgatatcagc   1380

acatcggcct ggtagcgatg ttcaggcaga acactggcat gtgggagtcc aacgctaatg   1440

tcaagggcac ccagatcggc gcctacttcg gggcctccct ctgctccgtg gacgtggaca   1500
```

-continued

```
gcaacggcag caccgacctg gtcctcatcg gggcccccca ttactacgag cagacccgag   1560
ggggccaggt gtccgtgtgc cccttgccca gggggagggc tcggtggcag tgtgatgctg   1620
ttctctacgg ggagcagggc caaccctggg gccgctttgg ggcagcccta acagtgctgg   1680
gggacgtaaa tggggacaag ctgacggacg tggccattgg ggccccagga gaggaggaca   1740
accggggtgc tgtttacctg tttcacggaa cctcaggatc tggcatcagc ccctcccata   1800
gccagcggat agcaggctcc aagctctctc ccaggctcca gtattttggt cagtcactga   1860
gtgggggcca ggacctcaca atggatggac tggtagacct gactgtagga gcccaggggc   1920
acgtgctgct gctcaggtcc cagccagtac tgagagtcaa ggcaatcatg gagttcaatc   1980
ccagggaagt ggcaaggaat gtatttgagt gtaatgatca ggtggtgaaa ggcaaggaag   2040
ccggagaggt cagagtctgc ctccatgtcc agaagagcac acgggatcgg ctaagagaag   2100
gacagatcca gagtgttgtg acttatgacc tggctctgga ctccggccgc ccacattccc   2160
gcgccgtctt caatgagaca aagaacagca cacgcagaca gacacaggtc ttggggctga   2220
cccagacttg tgagaccctg aaactacagt tgccgaattg catcgaggac ccagtgagcc   2280
ccattgtgct gcgcctgaac ttctctctgg tgggaacgcc attgtctgct ttcgggaacc   2340
tccggccagt gctggcggag gatgctcaga gactcttcac agccttgttt ccctttgaga   2400
agaattgtgg caatgacaac atctgccagg atgacctcag catcaccttc agtttcatga   2460
gcctggactg cctcgtggtg ggtgggcccc gggagttcaa cgtgacagtg actgtgagaa   2520
atgatggtga ggactcctac aggacacagg tcaccttctt cttcccgctt gacctgtcct   2580
accggaaggt gtccacgctc cagaaccagc gctcacagcg atcctggcgc ctggcctgtg   2640
agtctgcctc ctccaccgaa gtgtctgggg ccttgaagag caccagctgc agcataaacc   2700
accccatctt cccggaaaac tcagaggtca cctttaatat cacgtttgat gtagactcta   2760
aggcttccct tggaaacaaa ctgctcctca aggccaatgt gaccagtgag aacaacatgc   2820
ccagaaccaa caaaaccgaa ttccaactgg agctgccggt gaaatatgct gtctacatgg   2880
tggtcaccag ccatggggtc tccactaaat atctcaactt cacggcctca gagaatacca   2940
gtcgggtcat gcagcatcaa tatcaggtca gcaacctggg gcagaggagc ctccccatca   3000
gcctggtgtt cttggtgccc gtccggctga accagactgt catatgggac cgcccccagg   3060
tcaccttctc cgagaacctc tcgagtacgt gccacaccaa ggagcgcttg ccctctcact   3120
ccgactttct ggctgagctt cggaaggccc ccgtggtgaa ctgctccatc gctgtctgcc   3180
agagaatcca gtgtgacatc ccgttctttg gcatccagga agaattcaat gctaccctca   3240
aaggcaacct ctcgtttgac tggtacatca agacctcgca taaccacctc ctgatcgtga   3300
gcacagctga gatcttgttt aacgattccg tgttcaccct gctgccggga caggggggcgt  3360
ttgtgaggtc ccagacggag accaaagtgg agccgttcga ggtccccaac cccctgccgc   3420
tcatcgtggg cagctctgtc gggggactgc tgctcctggc cctcatcacc gccgcgctgt   3480
acaagctcgg cttcttcaag cggcaataca aggacatgat gagtgaaggg ggtcccccgg   3540
gggccgaacc ccagtagcgg ctccttcccg acagagctgc ctctcggtgg ccagcaggac   3600
tctgcccaga ccacacgtag cccccaggct gctggacacg tcggacagcg aagtatcccc   3660
gacaggacgg gcttgggctt ccatttgtgt gtgtgcaagt gtgtatgtgc gtgtgtgcaa   3720
gtgtctgtgt gcaagtgtgt gcacatgtgt gcgtgtgcgt gcatgtgcac ttgcacgccc   3780
atgtgtgagt gtgtgcaagt atgtgagtgt gtccaagtgt gtgtgcgtgt gtccatgtgt   3840
gtgcaagtgt gtgcatgtgt gcgagtgtgt gcatgtgtgt gctcaggggc gtgtggctca   3900
```

cgtgtgtgac tcagatgtct ctggcgtgtg ggtaggtgac ggcagcgtag cctctccggc 3960
agaagggaac tgcctgggct cccttgtgcg tgggtgaagc cgctgctggg ttttcctccg 4020
ggagagggga cggtcaatcc tgtgggtgaa gacagaggga aacacagcag cttctctcca 4080
ctgaaagaag tgggacttcc cgtcgcctgc gagcctgcgg cctgctggag cctgcgcagc 4140
ttggatggag actccatgag aagccgtggg tggaaccagg aacctcctcc acaccagcgc 4200
tgatgcccaa taaagatgcc cactgaggaa tgatgaagct tcctttctgg attcatttat 4260
tatttcaatg tgactttaat tttttggatg gataagcttg tctatggtac aaaaatcaca 4320
aggcattcaa gtgtacagtg aaaagtctcc ctttccagat attcaagtca cctccttaaa 4380
ggtagtcaag attgtgtttt gaggtttcct tcagacagat tccaggcgat gtgcaagtgt 4440
atgcacgtgt gcacacacac cacacataca cacacacaag ctttttttaca caaatggtag 4500 catactttat attggtctgt atcttgcttt ttttcaccaa tatttctcag acatcggttc 4560
atattaagac ataaattact ttttcattct tttataccgc tgcatagtat tccattgtgt 4620
gagtgtacca taatgtattt aaccagtctt cttttgatat actattttca ttctcttgtt 4680
attgcatcaa tgctgagtta ataaatcaaa tatatgtcat ttttgcatat atgtaaggat 4740
aa 4742

<210> SEQ ID NO 7
<211> LENGTH: 5188
<212> TYPE: DNA
<213> ORGANISM: Homo sapiens

<400> SEQUENCE: 7
aaaaccctgc aggagactgc gagccctgca gaactgctag ctgcggggga gagggcaggg 60
gtcgggcgcc tgtggcggag ccgggctggg gccagggcag ggaggctgac aagcggcggg 120
agaagccggc ggagggcggg atcgcgcctc ctgacatgtt gggggtatcc ctggccgggc 180
cgggccgggg ctaagagcgg cgctgcgggc cggggtcggg gtcgggtcgc ggtccgcccc 240
cgctgtccct ccgtcctgcc ctgtcgagga cgtgcgttcc gcactcggcc gcctccagag 300
ggagcgaggg aagcggctag aggatcgggg agaaggagca ttcgccggag gctggaggag 360
gctgacccgc gtccccgccc agcctgctcc tatgcggtac ttgaaggatg gcgaagaggt 420
cgcgcagtga ggatgaggat gatgaccttc agtatgccga tcatgattat gaagtaccac 480
aacaaaaagg actgaagaaa ctctggaaca gagtaaaatg gacaagggac gaggatgata 540
aattaaagaa gttggttgaa caacatggaa ctgatgattg gactctaatt gctagtcatc 600
ttcaaaatcg ctctgatttt cagtgccagc atcgatggca gaaagtttta aatcctgaat 660
tgataaaggg tccttggact aaagaagaag atcagagggt tattgaatta gttcagaaat 720
atgggccaaa aagatggtct ttaattgcaa aacatttaaa aggaagaata ggcaagcagt 780
gtagagaaag atggcataat catctgaatc ctgaggtaaa gaaatcttcc tggacagaag 840
aggaggacag gatcatctat gaagcacata agcggttggg aaatcgttgg gcagaaattg 900
ccaaactact tccaggaagg actgataatt ctatcaaaaa tcattggaat tctactatgc 960
gaagaaaagt ggaacaggag ggctatttac aagatggaat aaaatcagaa cgatcttcat 1020
ctaaacttca acacaaacct tgtgcagcta tggatcatat gcaaacccag aatcagtttt 1080
acatacctgt tcagatccct gggtatcagt atgtgtcacc tgaaggcaat tgtatagaac 1140
atgttcagcc tacttctgcc tttattcagc aacccttcat tgatgaagat cctgataagg 1200

-continued

```
aaaagaaaat aaaggaactt gagatgcttc ttatgtcagc tgagaatgaa gttagaagaa   1260
agcgaattcc atcacagcct ggaagttttt ctagctggtc tggtagtttc ctcatggatg   1320
ataacatgtc taatactcta aatagccttg acgagcacac tagtgagttt tacagtatgg   1380
atgaaaatca gcctgtgtct gctcagcaga attcacccac aaagttcctg gccgtggagg   1440
caaacgctgt gttatcctct ttgcagacca tcccagaatt tgcagagact ctagaactta   1500
ttgaatctga tcctgtagca tggagtgacg ttaccagttt tgatatttct gatgctgctg   1560
cttctcctat caaatccacc ccagttaaat taatgagaat tcagcacaat gaaggagcca   1620
tggaatgcca atttaacgtc agtcttgtac ttgaagggaa aaaaaacact tgtaatggtg   1680
gcaacagtga agctgttcct ttaacatccc caaatatagc caagtttagc actccaccag   1740
ccatcctcag aaagaagaga aaaatgcgag tgggtcattc cccaggcagc gaacttaggg   1800
atggctcatt gaacgatggt ggtaatatgg cgctaaaaca tacaccactg aaaacactac   1860
cattttctcc ttcacagttt ttcaacacat gtcctggtaa tgaacaactt aatatagaaa   1920
atccttcatt tacatcaacc cctatttgtg ggcagaaagc tctcattaca actcctcttc   1980
ataaggaaac aactcccaaa gatcaaaagg aaaatgtagg gtttagaaca cctactatta   2040
gaagatctat actgggtacc acaccaagaa ctcctactcc ttttaagaat gcgcttgctg   2100
ctcaggagaa aaaatatgga cctcttaaaa ttgtgtccca gccacttgct ttcttggaag   2160
aagatattcg ggaagtttta aaagaagaaa ctggaacaga cctattcctc aaagaggaag   2220
atgaacctgc ttacaaaagc tgcaaacaag agaataccgc ttctgggaag aaagtcagaa   2280
aatcactagt cttagataat tgggaaaaag aagaatcagg cactcaactg ttgactgaag   2340
acatttcaga catgcagtca gaaaatagat ttactacatc cttattaatg ataccattat   2400
tggaaataca tgacaatagg tgcaacttga ttcctgaaaa acaagatata aattcaacca   2460
acaaaacata tacacttact aaaaagaaac caaaccctaa cacttccaaa gttgtcaaat   2520
tggaaaagaa tcttcagtca aattgtgaat gggaaacagt ggtttatggg aagacagaag   2580
accaacttat tatgactgaa caagcaagaa gatatctgag tacttacaca gctaccagta   2640
gtacttcaag agctctcata ctgtaattgt tattaaaatt gatgaaatgc cccactccct   2700
tactgcagtc tctactaaat taggttgcag tgaaattttt ctcaattagt tgtttttaaa   2760
gttgtaagat agccctttta atacagcatc ttttttctat tctatatagt aggcagaaag   2820
ctagtaagtc acttaagggg tagatagttt catagtttat tttttaagag atgagatttt   2880
taaaaattgt tttaaagaa caagatggga aaataataga atgttcatgg atttctaaaa   2940
gtaaattctc atatattttc ttcacaagat atatgttgct actctcttga tgctgcagtt   3000
ttgttataga taggtgtatg agtatatatg atttctgaaa ttagtctatg tatggaaagc   3060
acacatgatt ttatgaagta cttttgccca tgtgctgatt tacttaggct accatttaca   3120
aagaaacaca ttgaaaagga atttaaagga aggatagaaa gttgcactac taattttttg   3180
ttttttttt cagaagcagt aaaattaact acagtgttaa atgtatttat ttgagcatag   3240
tactgaaaac aaaaagcatt caaaaaagag ttttttcttt attagtaaat agtattttct   3300
taatctcaga ggagctgaga gttttgttga atgtattgta cagtatgtag gagcaggaga   3360
actttgtaaa ttggaaagaa gtctgttttt ataatttatt tttattttta aagcttaaat   3420
gtagatattt atacgtatac agggtgccta gaagccaatg ttgtttcctg ttattacagc   3480
taacacagta aagaataatt ttgactttaa gtatgaaaca gtagtaagtt atagctgcaa   3540
agaatacaat atctatactg tatgtcacat ctacctaaat gttgcactat gccctttaaa   3600
```

```
tcatgctggt tataaagtag ttctaaaaat gtactaaata ataatttaat attttctttt   3660
taaattatat cgggggtggt catatacatt aatctggtga tttgtatatg tgtttgaaat   3720
ttttgcattt tgtttaaaaa ataatatggt accttggtcc ctaaaaacag tctgcactta   3780
gaagtttata tttactcagt gtttcagaag tggagaacat tatcttttat ttataaaaat   3840
attttgtcct tttttaaatg ttttgtgttt ctctacaggt tacaacagtt gcttcagttg   3900
cctgttttag gtgtttgcac ttattttatt tcttcttgaa agaattttta tttgcttttg   3960
tggtagagat tatatgtaat ttttttcag tcatataatg gtgtgctgtc aacttaaaca   4020
ctgacaggta aatagaattg tacactgtag tttgaattat ttataattga cacactctct   4080
ccctctccac tcctgaagta tgctgctata gaaaatagca gaatcggctt gctgctacga   4140
gagaaggaaa gagcgaccac cacttgcact gtgtgaaaag ataaaaaaca aatgatggca   4200
agttctcaag ttaactaaat ggaatcaacc attaccaggc aaattcttgc aaataccaaa   4260
atactactat gccttataaa acaaaatgaa agcaggttaa gattttctgc tctgtttgta   4320
tgttaataga aatggaaata ctaagtattt taatgcttag ctcttgaaca gtagacctaa   4380
aagggtttta agctatttaa atctacttgc tagtttttgc atattttata tatatatata   4440
tttatatata tatatagtga gaagtgaaga aaatgtatgg tactaagatt atgccttatt   4500
gataaataga taaaccaatt tgaatcctct tagcatgttt aagtatgttg attgctttct   4560
aattaatgaa cttctcacag aaatttcact tagtgaaacc aatgattgta gcaaactcat   4620
actggatcat ttcagttacc ttgaactaat agcacataat ggtttttgt tgttgttgtt   4680
tttaatgtag cccttacctg gatatacata gtctgcaatc accaaagtat aatatcttgt   4740
aaggctatat tttttaaagc atattttttc ttgagcatta aattatccta aatggtaata   4800
tattgtggat aagtctgggc ttattggaca taatacatat ttgggttggt actggttgaa   4860
tccttcagtt aactgctttg ttgctttttg caagattttt tatcttaaac atgtcaggca   4920
tcttaagtca cctttatact gttttgttcc tctgagtttc tttcagtatg ttatacaaat   4980
gccagacata acatgtagca gccatacttg catggaaact gactacacat acataatact   5040
gcattttatt gtaaggtttt cacattaata cagcaattac cctgactaaa ttgagttttg   5100
tgatatatgg aaaacttcat tgtaagagaa tcttgcatac aatgttgaca tattaacatc   5160
caaaataaag catctgtgta caagctga                                      5188
```

<210> SEQ ID NO 8
<211> LENGTH: 5008
<212> TYPE: DNA
<213> ORGANISM: Homo sapiens

<400> SEQUENCE: 8

```
aaaaccctgc aggagactgc gagccctgca gaactgctag ctgcggggga gagggcaggg     60
gtcgggcgcc tgtggcggag ccgggctggg gccagggcag ggaggctgac aagcggcggg    120
agaagccggc ggagggcggg atcgcgcctc ctgacatgtt gggggtatcc ctggccgggc    180
cgggccgggg ctaagagcgg cgctgcgggc cggggtcggg gtcgggtcgc ggtccgcccc    240
cgctgtccct ccgtcctgcc ctgtcgagga cgtgcgttcc gcactcggcc gcctccagag    300
ggagcgaggg aagcggctag aggatcgggg agaaggagca ttcgccggag gctggaggag    360
gctgacccgc gtccccgccc agcctgctcc tatgcggtac ttgaaggatg gcgaagaggt    420
cgcgcagtga ggatgaggat gatgaccttc agtatgccga tcatgattat gaagtaccac    480
```

-continued

```
aacaaaaagg actgaagaaa ctctggaaca gagtaaaatg gacaagggac gaggatgata    540
aattaaagaa gttggttgaa caacatggaa ctgatgattg gactctaatt gctagtcatc    600
ttcaaaatcg ctctgatttt cagtgccagc atcgatggca gaaagtttta aatcctgaat    660
tgataaaggg tccttggact aaagaagaag atcagagggt tattgaatta gttcagaaat    720
atgggccaaa aagatggtct ttaattgcaa aacatttaaa aggaagaata ggcaagcagt    780
gtagagaaag atggcataat catctgaatc ctgaggtaaa gaaatcttcc tggacagaag    840
aggaggacag gatcatctat gaagcacata agcggttggg aaatcgttgg gcagaaattg    900
ccaaactact tccaggaagg actgataatt ctatcaaaaa tcattggaat tctactatgc    960
gaagaaaagt ggaacaggag ggctatttac aagatggaat aaaatcagaa cgatcttcat   1020
ctaaacttca acacaaacct tgtgcagcta tggatcatat gcaaacccag aatcagtttt   1080
acatacctgt tcagatccct gggtatcagt atgtgtcacc tgaaggcaat tgtatagaac   1140
atgttcagcc tacttctgcc tttattcagc aacccttcat tgatgaagat cctgataagg   1200
aaaagaaaat aaaggaactt gagatgcttc ttatgtcagc tgagaatgaa gttagaagaa   1260
agcgaattcc atcacagcct ggaagttttt ctagctggtc tggtagtttc ctcatggatg   1320
ataacatgtc taatactcta aatagccttg acgagcacac tagtgagttt tacagtatgg   1380
atgaaaatca gcctgtgtct gctcagcaga attcacccac aaagttcctg gccgtggagg   1440
caaacgctgt gttatcctct ttgcagacca tcccagaatt tgcagagact ctagaactta   1500
ttgaatctga tcctgtagca tggagtgacg ttaccagttt tgatatttct gatgctgctg   1560
cttctcctat caaatccacc ccagttaaat taatgagaat tcagcacaat gaaggagcca   1620
tggaatgcca atttaacgtc agtcttgtac ttgaagggaa aaaaaacact tgtaatggtg   1680
gcaacagtga agctgttcct ttaacatccc caaatatagc caagtttagc actccaccag   1740
ccatcctcag aaagaagaga aaaatgcgag tgggtcattc cccaggcagc gaacttaggg   1800
atggctcatt gaacgatggt ggtaatatgg cgctaaaaca tacaccactg aaaacactac   1860
cattttctcc ttcacagttt ttcaacacat gtcctggtaa tgaacaactt aatatagaaa   1920
atccttcatt tacatcaacc cctatttgtg ggcagaaagc tctcattaca actcctcttc   1980
ataaggaaac aactcccaaa gatcaaaagg aaaatgtagg gtttagaaca cctactatta   2040
gaagatctat actgggtacc acaccaagaa ctcctactcc ttttaagaat gcgcttgctg   2100
ctcaggagaa aaaatatgga cctcttaaaa ttgtgtccca gccacttgct ttcttggaag   2160
aagatattcg ggaagtttta aaagaagaaa ctggaacaga cctattcctc aaagaggaag   2220
atgaacctgc ttacaaaagc tgcaaacaag agaataccgc ttctgggaag aaagtcagaa   2280
aatcactagt cttagataat tgggaaaaag aagaatcagg cactcaactg ttgactgaag   2340
acatttcaga catgcagtca aattgtgaat gggaaacagt ggtttatggg aagacagaag   2400
accaacttat tatgactgaa caagcaagaa gatatctgag tacttacaca gctaccagta   2460
gtacttcaag agctctcata ctgtaattgt tattaaaatt gatgaaatgc cccactccct   2520
tactgcagtc tctactaaat taggttgcag tgaaattttt ctcaattagt tgtttttaaa   2580
gttgtaagat agccctttta atacagcatc ttttttctat tctatatagt aggcagaaag   2640
ctagtaagtc acttaagggg tagatagttt catagtttat tttttaagag atgagatttt   2700
taaaaattgt ttttaaagaa caagatggga aaataataga atgttcatgg atttctaaaa   2760
gtaaattctc atatattttc ttcacaagat atatgttgct actctcttga tgctgcagtt   2820
ttgttataga taggtgtatg agtatatatg atttctgaaa ttagtctatg tatggaaagc   2880
```

```
acacatgatt ttatgaagta cttttgccca tgtgctgatt tacttaggct accatttaca   2940
aagaaacaca ttgaaaagga atttaaagga aggatagaaa gttgcactac taattttttg   3000
ttttttttt cagaagcagt aaaattaact acagtgttaa atgtatttat ttgagcatag   3060
tactgaaaac aaaaagcatt caaaaaagag tttttcttt attagtaaat agtattttct   3120
taatctcaga ggagctgaga gttttgttga atgtattgta cagtatgtag gagcaggaga   3180
actttgtaaa ttggaaagaa gtctgttttt ataatttatt tttattttta aagcttaaat   3240
gtagatattt atacgtatac agggtgccta gaagccaatg ttgtttcctg ttattacagc   3300
taacacagta aagaataatt ttgactttaa gtatgaaaca gtagtaagtt atagctgcaa   3360
agaatacaat atctatactg tatgtcacat ctacctaaat gttgcactat gccctttaaa   3420
tcatgctggt tataaagtag ttctaaaaat gtactaaata ataatttaat attttctttt   3480
taaattatat cgggggtggt catatacatt aatctggtga tttgtatatg tgtttgaaat   3540
ttttgcattt tgtttaaaaa ataatatggt accttggtcc ctaaaaacag tctgcactta   3600
gaagtttata tttactcagt gtttcagaag tggagaacat tatcttttat ttataaaaat   3660
attttgtcct tttttaaatg ttttgtgttt ctctacaggt tacaacagtt gcttcagttg   3720
cctgttttag gtgtttgcac ttattttatt tcttcttgaa agaattttta tttgcttttg   3780
tggtagagat tatatgtaat ttttttcag tcatataatg gtgtgctgtc aacttaaaca   3840
ctgacaggta aatagaattg tacactgtag tttgaattat ttataattga cacactctct   3900
ccctctccac tcctgaagta tgctgctata gaaaatagca gaatcggctt gctgctacga   3960
gagaaggaaa gagcgaccac cacttgcact gtgtgaaaag ataaaaaaca aatgatggca   4020
agttctcaag ttaactaaat ggaatcaacc attaccaggc aaattcttgc aaataccaaa   4080
atactactat gccttataaa acaaaatgaa agcaggttaa gattttctgc tctgtttgta   4140
tgttaataga aatggaaata ctaagtattt taatgcttag ctcttgaaca gtagacctaa   4200
aagggtttta agctatttaa atctacttgc tagtttttgc atattttata tatatatata   4260
tttatatata tatatagtga gaagtgaaga aaatgtatgg tactaagatt atgccttatt   4320
gataaataga taaaccaatt tgaatcctct tagcatgttt aagtatgttg attgctttct   4380
aattaatgaa cttctcacag aaatttcact tagtgaaacc aatgattgta gcaaactcat   4440
actggatcat ttcagttacc ttgaactaat agcacataat ggttttttgt tgttgttgtt   4500
tttaatgtag cccttacctg gatatacata gtctgcaatc accaaagtat aatatcttgt   4560
aaggctatat tttttaaagc atattttttc ttgagcatta aattatccta aatggtaata   4620
tattgtggat aagtctgggc ttattggaca taatacatat ttgggttggt actggttgaa   4680
tccttcagtt aactgctttg ttgctttttg caagattttt tatcttaaac atgtcaggca   4740
tcttaagtca cctttatact gttttgttcc tctgagtttc tttcagtatg ttatacaaat   4800
gccagacata acatgtagca gccatacttg catggaaact gactacacat acataatact   4860
gcattttatt gtaaggtttt cacattaata cagcaattac cctgactaaa ttgagttttg   4920
tgatatatgg aaaacttcat tgtaagagaa tcttgcatac aatgttgaca tattaacatc   4980
caaaataaag catctgtgta caagctga                                      5008
```

<210> SEQ ID NO 9
<211> LENGTH: 2632
<212> TYPE: DNA
<213> ORGANISM: Homo sapiens

<400> SEQUENCE: 9

```
agctgaggga cgcgtcagcc aggcaccccg gggtgtggcc agaggacttc ggcgacgctt     60
ccccgagagt agcccccctc ctcaacccag aaaagacaac cccgcggggc tgcagcgagc    120
caggcatgct cactggcgca ggcccggccc gcagcccgag caggaagcgc cggcgctagg    180
cggccccctg cgctgccagc tggagccggg cggagccagc gccccggcgc agggtggctc    240
tgccagtccc cgcgcgcctg ggcggccgca cacgtgtcca ggcgtcacgt ccgcgcgcgc    300
ccccggggct tgcgtcagcg gctgttccag aagcgggtgg gccagggctc tgcgcaccgc    360
tggggttcgg ggcccgggac gccgccggga ggagggcacc gcgcggggtc cgacgcggag    420
gcgtgctcgg aacgccgggg gctgcggagt gcatcagcgc ggtccagccc tccgcctgcc    480
gggcgccgag cgtctccgcc gcccggacct gggctgggcg ccgtggcgtt gcctcggagc    540
tcgctgcccg cggggcgcgc accgccttga cccgggcggc cccgcggcag gcaggcgccc    600
gcagttccat ggttggttcg gagcgcgatg agccgcccgt cctccaccgg ccccagcgct    660
aataaaccct gcagcaagca gccgccgccg cagccccagc acactccgtc cccggctgcg    720
cccccggccg ccgccaccat ctcggctgcg ggccccggct cgtccgcggt gcccgccgcg    780
gcggcggtga tctcgggccc cggcggcggc ggcggggccg gcccggtgtc cccgcagcac    840
cacgagctga cctcgctctt cgagtgtccg gtctgctttg actatgtcct gcctcctatt    900
ctgcagtgcc aggccgggca cctggtgtgt aaccaatgcc gccagaagtt gagctgctgc    960
ccgacgtgca ggggcgccct gacgcccagc atcaggaacc tggctatgga gaaggtggcc   1020
tcggcagtcc tgtttccctg taagtatgcc accacgggct gttccctgac cctgcaccat   1080
acggagaaac cagaacatga agacatatgt gaataccgtc cctactcctg cccatgtcct   1140
ggtgcttcct gcaagtggca ggggtccctg gaagctgtga tgtcccatct catgcacgcc   1200
cacaagagca ttaccaccct tcagggagaa gacatcgtct ttctagctac agacattaac   1260
ttgccagggg ctgtcgactg ggtgatgatg cagtcatgtt ttggccatca cttcatgctg   1320
gtgctggaga aacaagagaa gtacgaaggc caccagcagt tttttgccat cgtcctgctc   1380
attggcaccc gcaagcaagc cgagaacttt gcctacagac tggagttgaa tgggaaccgg   1440
cggagattga cctgggaggc cacgccccgt tcgattcatg acggtgtggc tgcggccatc   1500
atgaacagcg actgccttgt tttcgacaca gccatagcac atctttttgc agataatggg   1560
aaccttggaa tcaatgttac tatttctaca tgttgtccat gatgtgactt tcgtaaacct   1620
tcaaaattat ttgggcatag tgctctatgt ttaataaagg tttttataga tgttttattc   1680
catatgtctt cacaagtcag gacccacaat tacccgtgtt ttgtttgaac agcagtgtcc   1740
catctggctt cgacccaaca aagttcatta acctgggatg aatggggttg gcctgttggt   1800
gatttggatg ctgttctgtg atctaaaaca actcttattg aattgtattt actccctaaa   1860
caacacttga caggctgttg cacagggctt ctatagatca gtgtgttagg aatgggaggc   1920
cccttcctgc ctgccttccc atattggtcc cttgacattg acaaaagcac agtgactgtc   1980
agcagattcc tttacttttg tttgtgggag gtaggaattg ttttaatgca ttttaaacag   2040
tgtttctgaa attggatggc tggctaatag acactgaatc acccggagtg cttatcttaa   2100
aattgcagat ttagggagcc tgccaattta acagtctcat caggtgattc ttttcaacag   2160
taatgtttga gaattactgg gttaaattgt gggaaagggt ccagatttta aaggtgcttt   2220
aaggttgccc tctgccgata ctgtttgtct ttctactgtt tcatccccta acttccccca   2280
accctcaaat taaaactaga actatagatc cacatgaacg cacgcctgag atttggccac   2340
```

```
tcacctatgt tttgggtgga ttgcctagga aagcaagtca tatggccatt gatagttctc   2400

atgtaattag ttttgctcac cactagtaca gatgacccgt ttacacgtgg cttccctcgg   2460

aagccctcct caacagtagc tggtgtgaaa gactaaatca gtagagttgg aaaagcttta   2520

taaccggtgt gtcatatgct tgctatttaa agctgtgtgt tggttttgtt tttctgccac   2580

attcactagt tttttaataa atattttcca aaaatggata aaaaaaaaaa aa           2632


<210> SEQ ID NO 10
<211> LENGTH: 894
<212> TYPE: DNA
<213> ORGANISM: Homo sapiens

<400> SEQUENCE: 10

gcccgtcttc gtgtctcctc cctccctcgc cttcctcctt cctagctcct ctcctccagg     60

gccagactga gcccaggttg atttcaggcg gacaccaata gactccacag cagctccagg    120

agcccagaca ccggcggcca gaagcaaggc taggagctgc tgcagccatg tcggccctca    180

gcctcctcat tctgggcctg ctcacggcag tgccacctgc cagctgtcag caaggcctgg    240

ggaaccttca gccctggatg cagggcctta tcgcggtggc cgtgttcctg gtcctcgttg    300

caatcgcctt tgcagtcaac cacttctggt gccaggagga gccggagcct gcacacatga    360

tcctgaccgt cggaaacaag gcagatggag tcctggtggg aacagatgga aggtactctt    420

cgatggcggc cagtttcagg tccagtgagc atgagaatgc ctatgagaat gtgcccgagg    480

aggaaggcaa ggtccgcagc accccgatgt aaccttctct gtggctccaa ccccaagact    540

cccaggcaca tgggatggat gtccagtgct accacccaag ccccctcctt ctttgtgtgg    600

aatctgcaat agtgggctga ctccctccag ccccatgccg gccctacccg cccttgaagt    660

atagccagcc aaggttggag ctcagaccgt gtctaggttg gggctcggct gtggccctgg    720

ggtctcctgc tcagctcaga agagccttct ggagaggaca gtcagctgag cacctcccat    780

cctgctcaca cgtccttccc cataactatg gaaatggccc taatttctgt gaaataaaga    840

ctttttgtat ttctggggct gaggctcagc aacagcccct caggcttcca gtga          894


<210> SEQ ID NO 11
<211> LENGTH: 5003
<212> TYPE: DNA
<213> ORGANISM: Homo sapiens

<400> SEQUENCE: 11

agttgggctc ccgcctggct gggaggcggg agggatcccg ctcctgttgt tttccgccgg     60

caggagtagg ctggcgggcg cagggggcgg ggtgcgccct ccctccccgg ccagggcgct    120

cgggagcggg gacccgagcc tgcagccgag ctccgctgcc ggccctggac actcggctca    180

gccaagcatc cttcctgggg gccgaggaag tggggccact ctgccgttcc gaggacctgg    240

gaggagccct cggtaccccg ggccccgggg ccctggggca cacacgtcca gcccagcccg    300

agcctgcgtt tcctgagccg ggatctgggg cgagatggcc gcaggcggca gtgcgcccga    360

gccccgcgtc ctcgtctgcc tcggggcgct cctggccggc tgggtcgccg taggattgga    420

ggctgttgtc attggagaag ttcatgagaa tgttactctg cactgtggca acatctcggg    480

actgaggggc caggtgacct ggtaccggaa caactcggag cctgtcttcc ttctctcgtc    540

caactctagc ctccggccag ctgagcctcg cttctctcta gtggatgcca cctccctgca    600

cattgaatcg ctgagcctgg gagatgaggg aatctacacc tgccaggaga tcctgaatgt    660
```

```
gactcagtgg ttccaagtgt ggctgcaggt ggccagcggc ccctatcaga ttgaggtcca    720
catcgtggcc accggcacac tccccaacgg caccctctac gcagccaggg gctcccaggt    780
ggacttcagc tgcaacagca gctccaggcc accacccgtg gttgaatggt ggttccaggc    840
cctgaattcc agcagcgagt cctttggcca caacctgaca gtcaactttt tctcactgtt    900
actgatatcg ccaaacctcc aagggaacta cacctgttta gccttgaatc agctcagcaa    960
gagacatcga aaggtgacca ccgagctcct ggtctactat ccccctccat cagctcccca   1020
gtgctgggca cagatggcat caggatcgtt catgttgcag cttacctgtc gctgggatgg   1080
gggatacccct gaccctgact tcctgtggat agaagagcca ggaggtgtaa tcgtggggaa   1140
gtcaaagctg gggggtggaaa tgctgagcga gtcccagctg tcggatggca agaagttcaa   1200
gtgtgttaca agccacatag ttgggccaga gtcgggcgcc agctgcatgg tgcagatcag   1260
gggtccctcc cttctctctg agcccatgaa gacttgcttc actgggggca atgtgacgct   1320
tacatgccag gtgtctgggg cctacccccc tgccaagatc ctgtggctga ggaaccttac   1380
ccagcccgag gtgatcatcc agcctagcag ccgccatctc attacccagg atggccagaa   1440
ctccaccctc actatccaca actgctccca ggacctggat gagggctact acatctgccg   1500
agctgacagc cctgtagggg tgagggagat ggaaatctgg ctgagtgtga aagaaccttt   1560
aaatatcggg gggattgtgg gaaccattgt gagcctcctt ctgctgggac tggccattat   1620
ctcagggctt ctgttgcatt atagccctgt gttctgctgg aaagtaggaa acacttccag   1680
gggacaaaac atggatgatg tcatggtttt ggtggattca gaagaggaag aggaggagga   1740
ggaggaggag gaggaagatg ctgcagtagg ggaacaggag ggagcacgtg agagagagga   1800
gttgccaaaa gaaataccta agcaggacca cattcacaga gtgaccgcct tggtgaatgg   1860
gaacatagaa cagatgggaa atggattcca ggatcttcaa gatgacagca gtgaggagca   1920
aagtgacatt gttcaagaag aagacaggcc agtctgaaga agaggatggt ccatggttgt   1980
cttgctctga aagcttggag agctacattg aagacgagct cttcattcag ctttgactcc   2040
acctgcaccc ctggcggggg cttgcactaa caatgtttgg gtctcagcaa aaaacaaaac   2100
caagcacaca catctttcct tccatgtatt gaaaaacatt ggtttgattt gctctaagtt   2160
ttcccaatga tgtttaaaag ctttgagaag gaaagctgct tggtgtctg aggtgccact   2220
tctgctgtga atcctggctt tatccaggtt gatctactgt gatagatgct gatttagagg   2280
gaacagaggt cagggaagca ctgggtcttg gtgccttttg ccgctttttt tttttttttt   2340
tttttttttt gagacggagt ctccctctat tgcccaggct ggagtgcaat ggcacgatct   2400
tggctcacca caacttctgc ctcccaggtt caagcgattc tcctgcctca gccacggcac   2460
cttgcaaata tcagctcctt ggaacaggtg aagttccagg taccaatgcc aatcagagga   2520
aggcagtttg gttcaggctt tggagttaga aacacctgaa gttgaatctg ggctctgttg   2580
cttccttctt tcatgggcta gagcacgact ctttacctct ctcttggcct caatttcctc   2640
acctgtaaaa tagatgagga agctgctcac ttattattgt ctcgttctga aagcttggaa   2700
agctacatcg aagatgagct cttcattcag ctttgatttg acctgtaccc ctggtggggg   2760
attgcactgg caacatttgg gtctcagcaa aaaaaccaag cacacacatc tttccttcca   2820
tttattgaaa aacatctttg taagatccat tcattgaaaa acataatcca tttattgaaa   2880
aatatctttg taagatcacc tgctaaatat gaaaatctga cttgaatttg tactctttaa   2940
agttgcgtat ctgctctagt gggcaggacc tagggcttaa aggggaactt cctttctcca   3000
tttctaagaa ctgggactct aaaatgagaa gctggttgtc tgaagtaacc ctgcaggtgt   3060
```

```
ggttggggaa ggtctgtttt cttggatgaa ggaactaaac taagcatatc agagcactgt   3120
cttaaccagt tttatttccc tggagataga attcttttaa aaagagttag ggagctggta   3180
ataggaagtg cctttcatta taactacatt ttgcagagct tcatatttat atacaagcct   3240
cctaggtgat acactgttag cttgcagact ttcctatgct tcatttctcc tgttgctttc   3300
aaagaaggca ggagacacgt ttaataacgg agtatctggt gataagaatt gcttgggcaa   3360
accagctcat ctggactctt tctcagtctt ggaagtggga agaggaaaac ttgtttcctt   3420
cctgcttctt aaggatattc tgagggtaca ctgatcaata acactaaatt tggaatgaaa   3480
ataccatgtg atgagtttag cctgctgatg cttccagtag atccttgtat agtttcaaga   3540
tttaagtttt ccgatttcat ataaatttct taaagtcgag gaccttataa gggtgcaatg   3600
gatgtttgct aaatatgaaa aactgacttg aatttgcact ctttaatgtt gcgtatctgc   3660
tctagtgggc aggacctagg gcttaaaggg gaacttcctt tctccaattc taggaactgg   3720
gactctaaaa tgagaagctg gttgtctgaa gtaaccctgc aggtgtggtt ggggaaggtc   3780
tgttttcttg gatgaaggga ttaaactgag caaatcacta gaagtatgcc ctgtcccctg   3840
ctcagaacac tggggagctc aagagtgggc tgcaatgtgc acccctcagg aatagctgtg   3900
aattgcaggt ctactggctt tttgcttttt gtcttttgct gcaaggtacc ccacgtactt   3960
aaccattctc aacagtgtaa atcagtgtca ttttagaatg agatactcag cttgcttcta   4020
aagtcactga attactgagt gagtctctcc tttagagtct tcggcaacca aattccagaa   4080
ttgaagagtc tactactcag aggcaacaag attaaaaaaa gaaaacacaa aaactgttga   4140
ggtgaaaaaa aaaaaaaacc ctagctagga acacagagaa tgttttgtag gatcactggg   4200
atattttcca caacttcctc ttctctagca cacacatctg ttgataggaa atatttgagg   4260
gtttttccac taccaaatgg gagcttcatg gtcctggtgt caaacactat aaacctttga   4320
ccagctgagc tgtgactgct gtcacatatc tgagtcctgt gtgcacagta atatcctggg   4380
tcaggtaaaa tccaggtctt caagttttaa ggattttttg aagaattcgg gcttctttaa   4440
gacgatccat gcccaaatcc acaagcttgt tgacagtgga ttacagtttg tgtggcaaag   4500
tccaagttgt tacactgtgc tttaaaaaaa atcttatctg catgtattgt taacttagag   4560
accatgagat ctatttatca ggaccaggaa gatacacact tcaggtccat tgcaactgac   4620
tttttttcttg tttttctcaa accctggtgg agcctgggaa gggggcctcc acaattctgt   4680
ggctttgata ttagccccaa ttctcacaag cacatacaag ccccataatt gccgcaggaa   4740
aacacaagat ggaaaattgc aataacccat gcactgagac ttagaaaatc atccttacta   4800
ggcaaaatgt attatgatgc aataagtgcc aactgatatt tctcacgttg ggactggcca   4860
ggaactgctg caaagaaaaa taagcagctc cttctccatt atttacattt taagatgtgg   4920
tggggggagg ttgggagaaa ttagttctga ggttatcata tgcctttttt aaaagataat   4980
ggaataaagc tatttttaag taa                                           5003
```

METHOD AND KIT FOR DETERMINING IN VITRO THE PROBABILITY FOR AN INDIVIDUAL TO SUFFER FROM COLORECTAL CANCER

FIELD OF THE INVENTION

The present invention relates to the detection of a colorectal cancer, especially to a method and kit for determining the probability to suffer from such a cancer.

BACKGROUND

Colorectal cancer (CRC), also called colon cancer or large bowel cancer is the fifth most common form of cancer in the United States, the fourth common cancer in China and the third leading cause of cancer-related death in Europe. The early detection of CRC is the key to successful treatment and patient survival and represents a major public health challenge. Indeed, CRC is often curable particularly when diagnosed at early stages. Several screening strategies are already in place in various countries. Conventional CRC screening tests include fecal occult blood test (FOBT), sigmoidoscopy, colonoscopy, double contrast barium enema, or digital rectal examination. All of them have advantages and limitations, but compliance remains less than expected mainly due to logistics or discomfort for the patients.

Search for peripheral blood biomarkers aimed at early detection of CRC became a focus since several years, especially for its convenience. Meantime, blood-based test feasibility was supported by very few studies, which have shown that gene biomarkers in blood could differentiate CRC patients from controls. These studies were based on the flow cytometry that is a technique for counting and examining microscopic particles, such as cells by suspending them in a stream of fluid and analyzing them by using an electronic detection apparatus.

The present inventors have found that differentially expressed genes represented important biomarkers in peripheral blood samples. They did not used classical technique of flow cytometry but the determination of differential expression of genes from whole blood. It is non usual to determine an expression level of genes via the analysis of transcripts in whole blood, because it is commonly admitted by the persons skilled in the art that it is very difficult to retrieve a specific information when it is diluted in a complex mixture of RNAs (total RNA) without a step of specific purification. An advantage of the present method is also to avoid this step of purification of RNA.

Accordingly, the present invention relates to a method for determining in vitro, in a peripheral blood sample, the probability for an individual to suffer from a colorectal cancer, the method comprising the steps of:

a) determining, in the peripheral blood sample, the amount of at least one expression product from at least one nucleic acid sequence and no more than 7 nucleic acid sequences, said nucleic acid sequence being selected from the sequences identified in SEQ ID NOs: 1 to 11, b) comparing the amount of said expression product determined in step a) with a reference amount of the expression product for a group of individuals previously diagnosed as colorectal cancer patients and with a reference amount of the expression product for a group of individuals previously verified as non colorectal cancer individuals, c) performing analysis of results of step b), wherein
 - if the result for the tested individual is close to or equal to the result obtained from the group of individuals previously diagnosed as colorectal cancer patients, then the tested individual is classified as a colorectal cancer patient, and
 - if the result for the tested individual is close to or equal to the result obtained from the group of individuals previously verified as non colorectal cancer individuals, then the tested individual is classified as a non colorectal individual.

The amount of the expression product is directly linked to the expression level of a gene defined by its nucleic acid sequence.

The expression level of at least one of the above nucleic acids is a sufficient information for determining if the individual is a CRC patient or not. But, in a preferred embodiment of the invention, in the step a), it is determined the amount of the expression products from nucleic acid sequences selected from the group consisting of SEQ ID NO: 1, SEQ ID NO: 2 or SEQ ID NO: 3 or SEQ ID NO: 4, SEQ ID NO: 5 or SEQ ID NO: 6, SEQ ID NO: 7 or SEQ ID NO: 8, SEQ ID NO: 9, SEQ ID NO: 10 and SEQ ID NO: 11.

The amount of expression product(s) from the nucleic acid(s) is determined by bringing the expression product(s) into contact with at least one binding partner specific for each expression product.

Expression product(s) means RNA transcript(s) or polypeptides(s). Accordingly, in the method of the invention, it is determined the amount of at least one RNA transcript or at least one polypeptide.

The term RNA transcripts is intended to mean total RNA, i.e, coding or non coding RNA directly obtained from the peripheral blood sample or indirectly obtained from the blood sample after cell lysis. Especially, total RNA comprises transfer RNAs (tRNA), messenger RNAs (mRNAs), such as the mRNAs transcribed from the target gene, but also transcribed from any other gene, and ribosomal RNAs.

By way of indication, when the RNA is intracellular RNA, it can be extracted from the cells present in the blood sample by a step of lysis of, in order to release the nucleic acids contained in the cells of the individual to be tested. By way of example, use may be made of the methods of lysis as described in patent applications: WO 00/05338 regarding mixed magnetic and mechanical lysis, WO 99/53304 regarding electrical lysis, WO 99/15321 regarding mechanical lysis. Those skilled in the art may use other well-known methods of lysis, such as thermal or osmotic shocks or chemical lyses using chaotropic agents such as guanidinium salts (U.S. Pat. No. 5,234,809). It is also possible to provide an additional step for separating the nucleic acids from the other cellular constituents released in the lysis step. This generally makes it possible to concentrate the nucleic acids.

In the method of the invention the RNA transcript can be detected and quantified by hybridization, amplification or sequencing. Especially, to be detected and quantified, the RNA transcript is brought into contact with at least one probe or at least one primer under predetermined conditions which enable hybridization of said probe and/or said primer to the RNA transcript. But in another embodiment of the invention, DNA copies of the RNA transcript are prepared and said DNA copies are determined by bringing them into contact with at least one probe or at least one primer under predetermined conditions which enable hybridization of said probe and/or said primer to the DNA copies.

More precisely, in the methods described above RNA transcript or DNA copies are brought into contact with at least one hybridization probe and at least one primer and more particularly at least one hybridization probe and two primers.

The term “hybridization” is intended to mean the process during which, under appropriate conditions, two nucleotide fragments bind with stable and specific hydrogen bonds so as to form a double-stranded complex. These hydrogen bonds form between the complementary adenine (A) and thymine (T) (or uracile (U)) bases (this is referred to as an A-T bond) or between the complementary guanine (G) and cytosine (C) bases (this is referred to as a G-C bond). The hybridization of two nucleotide fragments may be complete (reference is then made to complementary nucleotide fragments or sequences), i.e. the double-stranded complex obtained during this hybridization comprises only A-T bonds and C-G bonds. This hybridization may be partial (reference is then made to sufficiently complementary nucleotide fragments or sequences), i.e. the double-stranded complex obtained comprises A-T bonds and C-G bonds that make it possible to form the double-stranded complex, but also bases not bound to a complementary base. The hybridization between two nucleotide fragments depends on the working conditions that are used, and in particular on the stringency. The stringency is defined in particular as a function of the base composition of the two nucleotide fragments, and also by the degree of mismatching between two nucleotide fragments. The stringency can also depend on the reaction parameters, such as the concentration and the type of ionic species present in the hybridization solution, the nature and the concentration of denaturing agents and/or the hybridization temperature. All these data are well known and the appropriate conditions can be determined by those skilled in the art. In general, depending on the length of the nucleotide fragments that it is intended to hybridize, the hybridization temperature is between approximately 20 and 70.degree. C., in particular between 35 and 65.degree. C. in a saline solution at a concentration of approximately 0.5 to 1 M. A sequence, or nucleotide fragment, or oligonucleotide, or polynucleotide, is a series of nucleotide motifs assembled together by phosphoric ester bonds, characterized by the informational sequence of the natural nucleic acids, capable of hybridizing to a nucleotide fragment, it being possible for the series to contain monomers having different structures and to be obtained from a natural nucleic acid molecule and/or by genetic recombination and/or by chemical synthesis. A motif is a derivative of a monomer which may be a natural nucleotide of nucleic acid, the constitutive elements of which are a sugar, a phosphate group and a nitrogenous base; in DNA, the sugar is deoxy-2-ribose, in RNA, the sugar is ribose; depending on whether DNA or RNA is involved, the nitrogenous base is selected from adenine, guanine, uracile, cytosine and thymine; alternatively the monomer is a nucleotide that is modified in at least one of the three constitutive elements; by way of example, the modification may occur either at the level of the bases, with modified bases such as inosine, methyl-5-deoxycytidine, deoxyuridine, dimethylamino-5-deoxyuridine, diamino-2,6-purine, bromo-5-deoxyuridine or any other modified base capable of hybridization, or at the level of the sugar, for example the replacement of at least one deoxyribose with a polyamide (P. E. Nielsen et al, Science, 254, 1497-1500 (1991)), or else at the level of the phosphate group, for example its replacement with esters in particular selected from diphosphates, alkyl- and arylphosphonates and phosphorothioates.

For the purpose of the present invention, the term “amplification primer” is intended to mean a nucleotide fragment comprising from 5 to 100 nucleotides, preferably from 15 to 30 nucleotides that allow the initiation of an enzymatic polymerization, for instance an enzymatic amplification reaction. The term “enzymatic amplification reaction” is intended to mean a process which generates multiple copies of a nucleotide fragment through the action of at least one enzyme. Such amplification reactions are well known to those skilled in the art and mention may in particular be made of the following techniques: PCR (polymerase chain reaction), as described in U.S. Pat. No. 4,683,195, U.S. Pat. No. 4,683,202 and U.S. Pat. No. 4,800,159, LCR (ligase chain reaction), disclosed, for, example, in patent application EP 0 201 184, RCR (repair chain reaction), described in patent application WO 90/01069, 3SR (self sustained sequence replication) with patent application WO 90/06995, NASBA (nucleic acid sequence-based amplification) with patent application WO 91/02818, TMA (transcription mediated amplification) with U.S. Pat. No. 5,399,491 and RT-PCR.

When the enzymatic amplification is a PCR, it is used at least two amplification primers, specific for a target gene, that allow the amplification material specific for the target gene. The material specific for the target gene then preferably comprises a complementary DNA obtained by reverse transcription of messenger RNA derived from the target gene (reference is then made to target-gene-specific cDNA) or a complementary RNA obtained by transcription of the cDNAs specific for a target gene (reference is then made to target-gene-specific cRNA). When the enzymatic amplification is a PCR carried out after a reverse transcription reaction, reference is made to RT-PCR.

The term “hybridization probe” is intended to mean a nucleotide fragment comprising at least 5 nucleotides, such as from 5 to 100 nucleotides, in particular from 10 to 75 nucleotides, such as 15-35 nucleotides and 60-70 nucleotides, having a hybridization specificity under given conditions so as to form a hybridization complex with the material specific for a target gene. In the present invention, the material specific for the target gene may be a nucleotide sequence included in a messenger RNA derived from the target gene (reference is then made to target-gene-specific mRNA), a nucleotide sequence included in a complementary DNA obtained by reverse transcription of said messenger RNA (reference is then made to target-gene-specific cDNA), or else a nucleotide sequence included in a complementary RNA obtained by transcription of said cDNA as described above (reference will then be made to target-gene-specific cRNA). The hybridization probe may include a label for its detection. The term “detection” is intended to mean either a direct detection such as a counting method, or an indirect detection by a method of detection using a label. Many methods of detection exist for detecting nucleic acids (see, for example, Kricka et al., Clinical Chemistry, 1999, no 45 (4), p. 453-458 or Keller G. H. et al., DNA Probes, 2nd Ed., Stockton Press, 1993, sections 5 and 6, p. 173-249. The term “label” is intended to mean a tracer capable of generating a signal that can be detected. A non limiting list of these tracers includes enzymes which produce a signal that can be detected, for example, by colorimetry, fluorescence or luminescence, such as horseradish peroxidase, alkaline phosphatase, beta-galactosidase, glucose-6-phosphate dehydrogenase; chromophores such as fluorescent, luminescent or dye compounds; electron dense groups detectable by electron microscopy or by virtue of their electrical properties such as conductivity, by amperometry or voltametry methods, or by impedance measurement; groups that can be detected by optical methods such as diffraction, surface plasmon resonance, or contact angle variation, or by physical methods such as atomic force spectroscopy, tunnel effect, etc.; radioactive molecules such as $^{32}P$, $^{35}S$ or $^{125}I$.

For the purpose of the present invention, the hybridization probe may be a "detection" probe. In this case, the "detection" probe is labeled by means of a label. The detection probe may in particular be a "molecular beacon" detection probe as described by Tyagi & Kramer (Nature biotech, 1996, 14:303-308). These "molecular beacons" become fluorescent during the hybridization. They have a stem-loop-type structure and contain a fluorophore and a "quencher" group. The binding of the specific loop sequence with its complementary target nucleic acid sequence causes the stem to unroll and the emission of a fluorescent signal during excitation at the appropriate wavelength. The detection probe in particular may be a "reporter probe" comprising a "color-coded barecode" according to NanoString™'s technology.

For the detection of the hybridization reaction, use may be made of target sequences that have been labeled, directly (in particular by the incorporation of a label within the target sequence) or indirectly (in particular using a detection probe as defined above). It is in particular possible to carry out, before the hybridization step, a step consisting in labeling and/or cleaving the target sequence, for example using a labeled deoxyribonucleotide triphosphate during the enzymatic amplification reaction. The cleavage may be carried out in particular by the action of imidazole or of manganese chloride. The target sequence may also be labeled after the amplification step, for example by hybridizing a detection probe according to the sandwich hybridization technique described in document WO 91/19812. Another specific preferred method of labeling nucleic acids is described in application FR 2780059.

According to a preferred embodiment of the invention, the detection probe comprises a fluorophore and a quencher. According to an even more preferred embodiment of the invention, the hybridization probe comprises an FAM (6-carboxy-fluorescein) or ROX (6-carboxy-X-rhodamine) fluorophore at its 5' end and a quencher (Dabsyl) at its 3' end.

The hybridization probe may also be a "capture" probe. In this case, the "capture" probe is immobilized or can be immobilized on a solid substrate by any appropriate means, i.e. directly or indirectly, for example by covalence or adsorption. As solid substrate, use may be made of synthetic materials or natural materials, optionally chemically modified, in particular polysaccharides such as cellulose-based materials, for example paper, cellulose derivatives such as cellulose acetate and nitrocellulose or dextran, polymers, copolymers, in particular based on styrene-type monomers, natural fibers such as cotton, and synthetic fibers such as nylon; inorganic materials such as silica, quartz, glasses or ceramics; latices; magnetic particles; metal derivatives, gels, etc. The solid substrate may be in the form of a microtitration plate, of a membrane as described in application WO-A-94/12670 or of a particle. It is also possible to immobilize on the substrate several different capture probes, each being specific for a target gene. In particular, a biochip on which a large number of probes can be immobilized may be used as substrate. The term "biochip" is intended to mean a solid substrate that is small in size, to which a multitude of capture probes are attached at predetermined positions. The biochip, or DNA chip, concept dates from the beginning of the 1990s. It is based on a multidisciplinary technology that integrates microelectronics, nucleic acid chemistry, image analysis and information technology. The operating principle is based on a foundation of molecular biology: the hybridization phenomenon, i.e. the pairing, by complementarity, of the bases of two DNA and/or RNA sequences. The biochip method is based on the use of capture probes attached to a solid substrate, on which probes a sample of target nucleotide fragments directly or indirectly labeled with fluorochromes is made to act. The capture probes are positioned specifically on the substrate or chip and each hybridization gives a specific piece of information, in relation to the target nucleotide fragment. The pieces of information obtained are cumulative, and make it possible, for example, to quantify the level of expression of one or more target genes. In order to analyze the expression of a target gene, a substrate comprising a multitude of probes, which correspond to all or part of the target gene, which is transcribed to mRNA, can then be prepared. For the purpose of the present invention, the term "low-density substrate" is intended to mean a substrate comprising fewer than 50 probes. For the purpose of the present invention, the term "medium-density substrate" is intended to mean a substrate comprising from 50 probes to 10 000 probes. For the purpose of the present invention, the term "high-density substrate" is intended to mean a substrate comprising more than 10 000 probes.

The cRNAs or cDNAs specific for a nucleic acid of a target gene that it is desired to analyze are then hybridized, for example, to specific capture probes. After hybridization, the substrate or chip is washed and the labeled cDNA or cRNA/capture probe complexes are revealed by means of a high-affinity ligand bound, for example, to a fluorochrome-type label. The fluorescence is read, for example, with a scanner and the analysis of the fluorescence is processed by information technology. By way of indication, mention may be made of the DNA chips developed by the company Affymetrix ("Accessing Genetic Information with High-Density DNA arrays", M. Chee et al., Science, 1996, 274, 610-614. "Light-generated oligonucleotide arrays for rapid DNA sequence analysis", A. Caviani Pease et al., Proc. Natl. Acad. Sci. USA, 1994, 91, 5022-5026), for molecular diagnoses. In this technology, the capture probes are generally small in size, around 25 nucleotides. Other examples of biochips are given in the publications by G. Ramsay, Nature Biotechnology, 1998, No. 16, p. 40-44; F. Ginot, Human Mutation, 1997, No. 10, p. 1-10; J. Cheng et al, Molecular diagnosis, 1996, No. 1 (3), p. 183-200; T. Livache et al, Nucleic Acids Research, 1994, No. 22 (15), p. 2915-2921 J. Cheng et al, Nature Biotechnology, 1998, No. 16, p. 541-546 or in U.S. Pat. No. 4,981,783, U.S. Pat. No. 5,700,637, U.S. Pat. No. 5,445,934, U.S. Pat. No. 5,744,305 and U.S. Pat. No. 5,807,522. The main characteristic of the solid substrate should be to conserve the hybridization characteristics of the capture probes on the target nucleotide fragments while at the same time generating a minimum background noise for the method of detection. Three main types of fabrication can be distinguished for immobilizing the probes on the substrate.

First of all, there is a first technique which consists in depositing pre-synthesized probes. The attachment of the probes is carried out by direct transfer, by means of micropipettes or of microdots or by means of an inkjet device. This technique allows the attachment of probes having a size ranging from a few bases (5 to 10) up to relatively large sizes of 60 bases (printing) to a few hundred bases (microdeposition).

Printing is an adaptation of the method used by inkjet printers. It is based on the propulsion of very small spheres of fluid (volume<1 nl) at a rate that may reach 4000 drops/second. The printing does not involve any contact between the system releasing the fluid and the surface on which it is deposited.

Microdeposition consists in attaching long probes of a few tens to several hundred bases to the surface of a glass slide. These probes are generally extracted from databases and are in the form of amplified and purified products. This technique makes it possible to produce chips called microarrays that carry approximately ten thousand spots, called recognition zones, of DNA on a surface area of a little less than 4 cm.sup.2. The use of nylon membranes, referred to as "macroarrays", which carry products that have been amplified, generally by PCR, with a diameter of 0.5 to 1 mm and the maximum density of which is 25 spots/cm.sup.2, should not however be forgotten. This very flexible technique is used by many laboratories. In the present invention, the latter technique is considered to be included among biochips. A certain volume of sample can, however, be deposited at the bottom of a microtitration plate, in each well, as in the case in patent applications WO-A-00/71750 and FR 00/14896, or a certain number of drops that are separate from one another can be deposited at the bottom of one and the same Petri dish, according to another patent application, FR 00/14691.

The second technique for attaching the probes to the substrate or chip is called in situ synthesis. This technique results in the production of short probes directly at the surface of the chip. It is based on in situ oligonucleotide synthesis (see, in particular, patent applications WO 89/10977 and WO 90/03382) and is based on the oligonucleotide synthesizer process. It consists in moving a reaction chamber, in which the oligonucleotide extension reaction takes place, along the glass surface.

Finally, the third technique is called photolithography, which is a process that is responsible for the biochips developed by Affymetrix. It is also an in situ synthesis. Photolithography is derived from microprocessor techniques. The surface of the chip is modified by the attachment of photolabile chemical groups that can be light-activated. Once illuminated, these groups are capable of reacting with the 3' end of an oligonucleotide. By protecting this surface with masks of defined shapes, it is possible to selectively illuminate and therefore activate areas of the chip where it is desired to attach one or other of the four nucleotides. The successive use of different masks makes it possible to alternate cycles of protection/reaction and therefore to produce the oligonucleotide probes on spots of approximately a few tens of square micrometers ($\mu m^2$). This resolution makes it possible to create up to several hundred thousand spots on a surface area of a few square centimeters ($cm^2$). Photolithography has advantages: in bulk in parallel, it makes it possible to create a chip of N-mers in only 4.times.N cycles. All these techniques can be used with the present invention. According to a preferred embodiment of the invention, the at least one specific reagent of step b) defined above comprises at least one hybridization probe which is preferably immobilized on a substrate. This substrate is preferably a low-, high- or medium-density substrate as defined above.

These hybridization steps on a substrate comprising a multitude of probes may be preceded by an enzymatic amplification reaction step, as defined above, in order to increase the amount of target genetic material.

The determination of the expression level of a target gene can be carried out by any of the protocols known to those skilled in the art. In general, the expression of a target gene can be analyzed by detecting the mRNAs (messenger RNAs) that are transcribed from the target gene at a given moment.

The invention preferably relates to the determination of the expression level of a target gene by detection of the mRNAs derived from this target gene according to any of the protocols well known to those skilled in the art. According to a specific embodiment of the invention, the expression level of several target genes is determined simultaneously, by detection of several different mRNAs, each mRNA being derived from a target gene.

By way of amplification, it is possible, to determine the expression level of the target gene as follows: 1) After having extracted the total RNA (comprising the transfer RNAs (tRNAs), the ribosomal RNAs (rRNAs) and the messenger RNAs (mRNAs)) from the whole blood, a reverse transcription step is carried out in order to obtain the complementary DNAs (or cDNAs) of said mRNAs. By way of indication, this reverse transcription reaction can be carried out using a reverse transcriptase enzyme which makes it possible to obtain, from an RNA fragment, a complementary DNA fragment. The reverse transcriptase enzyme from AMV (Avian Myoblastosis Virus) or from MMLV (Moloney Murine Leukaemia Virus) can in particular be used. When it is more particularly desired to obtain only the cDNAs of the mRNAs, this reverse transcription step is carried out in the presence of nucleotide fragments comprising only thymine bases (polyT), which hybridize by complementarity to the polyA sequence of the mRNAs so as to form a polyT-polyA complex which then serves as a starting point for the reverse transcription reaction carried out by the reverse transcriptase enzyme. cDNAs complementary to the mRNAs derived from a target gene (target-gene-specific cDNA) and cDNAs complementary to the mRNAs derived from genes other than the target gene (cDNAs not specific for the target gene) are then obtained. 2) The amplification primer(s) specific for a target gene is (are) brought into contact with the target-gene-specific cDNAs and the cDNAs not specific for the target gene. The amplification primer(s) specific for a target gene hybridize(s) with the target-gene-specific cDNAs and a predetermined region, of known length, of the cDNAs originating from the mRNAs derived from the target gene is specifically amplified. The cDNAs not specific for the target gene are not amplified, whereas a large amount of target-gene-specific cDNAs is then obtained. For the purpose of the present invention, reference is made, without distinction, to "target-gene-specific cDNAs" or to "cDNAs originating from the mRNAs derived from the target gene". This step can be carried out in particular by means of a PCR-type amplification reaction or by any other amplification technique as defined above. By PCR, it is also possible to simultaneously amplify several different cDNAs, each one being specific for different target genes, by using several pairs of different amplification primers, each one being specific for a target gene: reference is then made to multiplex amplification. 3) The expression of the target gene is determined by detecting and quantifying the target-gene-specific cDNAs obtained in step 2) above. This detection can be carried out after electrophoretic migration of the target-gene-specific cDNAs according to their size. The gel and the medium for the migration can include ethidium bromide so as to allow direct detection of the target-gene-specific cDNAs when the gel is placed, after a given migration period, on a UV (ultraviolet)-ray light table, through the emission of a light signal. The greater the amount of target-gene-specific cDNAs, the brighter this light signal.

These electrophoresis techniques are well known to those skilled in the art. The target-gene-specific cDNAs can also be detected and quantified using a quantification range obtained by means of an amplification reaction carried out until saturation. In order to take into account the variability in enzymatic efficiency that may be observed during the various steps (reverse transcription, PCR, etc.), the expression of a target gene of various groups of patients can be normalized by simultaneously determining the expression of a "housekeeping" gene, the expression of which is similar in the various groups of patients. By realizing a ratio of the expression of the target gene to the expression of the housekeeping gene, i.e. by realizing a ratio of the amount of target-gene-specific cDNAs to the amount of housekeeping-gene-specific cDNAs, any variability between the various experiments is thus corrected. Those skilled in the art may refer in particular to the following publications: Bustin S A, J Mol Endocrinol, 2002, 29: 23-39; Giulietti A Methods, 2001, 25: 386-401.

By way of hybridization, the expression of a target gene can be determined as follows: 1) After having extracted the total RNA from the whole blood, a reverse transcription step is carried out as described above in order to obtain cDNAs complementary to the mRNAs derived from a target gene (target-gene-specific cDNA) and cDNAs complementary to the mRNAs derived from genes other than the target gene (cDNA not specific for the target gene). 2) All the cDNAs are brought into contact with a substrate, on which are immobilized capture probes specific for the target gene whose expression it is desired to analyze, in order to carry out a hybridization reaction between the target-gene-specific cDNAs and the capture probes, the cDNAs not specific for the target gene not hybridizing to the capture probes. The hybridization reaction can be carried out on a solid substrate which includes all the materials as indicated above. According to a preferred embodiment, the hybridization probe is immobilized on a substrate. Preferably, the substrate is a low-, high- or medium-density substrate as defined above. The hybridization reaction may be preceded by a step consisting of enzymatic amplification of the target-gene-specific cDNAs as described above, so as to obtain a large amount of target-gene-specific cDNAs and to increase the probability of a target-gene-specific cDNA hybridizing to a capture probe specific for the target gene. The hybridization reaction may also be preceded by a step consisting in labeling and/or cleaving the target-gene-specific cDNAs as described above, for example using a labeled deoxyribonucleotide triphosphate for the amplification reaction. The cleavage can be carried out in particular by the action of imidazole and manganese chloride. The target-gene-specific cDNA can also be labeled after the amplification step, for example by hybridizing a labeled probe according to the sandwich hybridization technique described in document WO-A-91/19812. Other preferred specific methods for labeling and/or cleaving nucleic acids are described in applications WO 99/65926, WO 01/44507, WO 01/44506, WO 02/090584, WO 02/090319. 3) A step consisting of detection of the hybridization reaction is subsequently carried out. The detection can be carried out by bringing the substrate on which the capture probes specific for the target gene are hybridized with the target-gene-specific cDNAs into contact with a "detection" probe labeled with a label, and detecting the signal emitted by the label. When the target-gene-specific cDNA has been labeled beforehand with a label, the signal emitted by the label is detected directly.

The expression of a target gene can also be determined in the following way: 1) After having extracted the total RNA from the whole blood, a reverse transcription step is carried out as described above in order to obtain the cDNAs of the mRNAs of the biological material. The polymerization of the complementary RNA of the cDNA is subsequently carried out using a T7 polymerase enzyme which functions under the control of a promoter and which makes it possible to obtain, from a DNA template, the complementary RNA. The cRNAs of the cDNAs of the mRNAs specific for the target gene (reference is then made to target-gene-specific cRNA) and the cRNAs of the cDNAs of the mRNAs not specific for the target gene are then obtained. 2) All the cRNAs are brought into contact with a substrate on which are immobilized capture probes specific for the target gene whose expression it is desired to analyze, in order to carry out a hybridization reaction between the target-gene-specific cRNAs and the capture probes, the cRNAs not specific for the target gene not hybridizing to the capture probes. When it is desired to simultaneously analyze the expression of several target genes, several different capture probes can be immobilized on the substrate, each one being specific for a target gene. The hybridization reaction may also be preceded by a step consisting in labeling and/or cleaving the target-gene-specific cRNAs as described above. 3) A step consisting of detection of the hybridization reaction is subsequently carried out. The detection can be carried out by bringing the substrate on which the capture probes specific for the target gene are hybridized with the target-gene-specific cRNA into contact with a "detection" probe labeled with a label, and detecting the signal emitted by the label. When the target-gene-specific cRNA has been labeled beforehand with a label, the signal emitted by the label is detected directly. The use of cRNA is particularly advantageous when a substrate of biochip type on which a large number of probes are hybridized is used.

When the expression product is a polypeptide it can be detected by bringing it in contact with at least one specific ligand, such as defined below. In a preferred embodiment the expressed polypeptide is brought into contact with at least two specific ligands, such as defined below. Specific ligand means for example an antibody or an affinity protein named "Nanofitin™".

Nanofitins are affinity proteins with competitive features. They present a competitive affinity, similar to antibodies.

The term "antibody or antibodies" embraces polyclonal antibodies, monoclonal antibodies, humanized antibodies, recombinant antibodies. Their production methods are well known by the person skilled in the art.

The present invention also includes a kit for determining in vitro the probability for an individual to suffer from a colorectal cancer comprising at least one binding partner specific for at least one nucleic acid sequence and no more than 7 binding partners specific for 7 expression products of 7 nucleic acid sequences, wherein the at least one binding partner is specific for at least one expression product of at least one nucleic acid sequence selected from the group consisting of sequences set forth in SEQ ID NOs: 1 to 11.

Especially, the kit comprises a combination of 7 binding partners which are specific for the expression products of 7 nucleic acid sequences having the sequences set forth in SEQ ID NOs: SEQ ID NO: 1, SEQ ID NO: 2 or SEQ ID NO: 3 or SEQ ID NO: 4, SEQ ID NO: 5 or SEQ ID NO: 6, SEQ ID NO: 7 or SEQ ID NO: 8, SEQ ID NO: 9, SEQ ID NO: 10 and SEQ ID NO: 11.

In the kit the specific binding partner comprises:

at least one hybridization probe, or at least one hybridization probe and at least one primer, or at least one hybridization probe and two primers, or at least one specific ligand or at least two specific ligands, such as antibody and/or affinity protein.

Finally, the invention concerns the use of at least one specific binding partner for at least one expression product of at least one nucleic acid sequence and no more than 7 specific binding partners for 7 expression products of 7 nucleic acid sequences, said at least one nucleic acid sequence having a sequence selected from the group consisting of nucleic acid sequences set forth in SEQ ID NOs 1 to 11, in the manufacture of a composition for determining in vitro the probability for an individual to suffer from a colorectal cancer.

Especially, the use of a combination of 7 specific binding partners which are specific for 7 expression products of 7 nucleic acid sequences having the sequences set forth in SEQ ID NOs: SEQ ID NO: 1, SEQ ID NO: 2 or SEQ ID NO: 3 or SEQ ID NO: 4, SEQ ID NO: 5 or SEQ ID NO: 6, SEQ ID NO: 7 or SEQ ID NO: 8, SEQ ID NO: 9, SEQ ID NO: 10 and SEQ ID NO: 11.

Specific binding partner comprises:

at least one hybridization probe, or at least one hybridization probe and at least one primer, or at least one hybridization probe and two primers, or at least one specific ligand or at least two specific ligands, such as antibody and/or affinity protein.

EXAMPLE

I) Materials and Methods

1. Patients and Sample Collection

Peripheral blood samples from 161 colorectal patients (CRC) and 148 colonoscopy negative control patients (CNCs) were collected, between 2006 and 2010. The CRC patients were recruited at the Department of Colorectal Surgery, FDUSCC, China. The tumors were staged according to the International Union Against Cancer (UICC) recommended tumor-node-metastasis (TNM) system. No patient received preoperative radiotherapy or chemotherapy. Patients suffering from hereditary colorectal cancer or inflammatory bowel disease (Crohn's disease or ulcerative colitis) were excluded from this study. The CNCs, without any symptom of polyps or colorectal cancer, which had been confirmed by colonoscopy, were enrolled from the Community Hospital in Shanghai area and FDUSCC. For each patient, 2.5 ml of peripheral blood were collected into PAXgene™ Blood RNA tubes (PreAnalytiX GmbH, Hombrechtikon, CH) and processed according to manufacturer's guidelines.

The study involves two separate cohorts of participants. Cohort 1 consists of 100 CRC patients and 100 CNCs. For CRC patients, blood samples were collected in FDUSCC at least one week after colonoscopy, before surgery. For CNCs, blood samples were collected in a Community Hospital in the Shanghai area one week before the colonoscopy. The gene expression profiles from these samples were analyzed as a train set to search for significant genes associated with CRC and identify molecular signature. Cohort 2 includes 61 CRC patients and 48 CNCs. Samples were collected in the same way as cohort 1. Cohort 2 was used as an independent test set to verify the signature performance that observed in the cohort 1.

2. RNA Extraction and Microarray Experiments

Total RNA was extracted with the PAXgene™ Blood RNA System (PreAnalytix) following manufacturer's instructions. The quantity of total RNA was measured by spectrophotometer at optical density 260 nanometers and the quality was assessed using the RNA 6000 Nano LabChip® Kit on a BioAnalyzer Agilent 2100 (Agilent Technologies, Palo Alto, Calif., U.S.A.). Only samples with RNA Integrity Number between 7 and 10 were analyzed. 50 nanograms of total RNA was then reversely transcripted and linearly amplified to single strand cDNA using Ribo-SPIA™ technology with WT-Ovation™ RNA Amplification System (NuGEN Technologies Inc., San Carlos, Calif., U.S.A.) according to the manufacturer's standard protocol, and the products were purified with QIAquick™ PCR purification kit (QIAGEN GmbH, Hilden, Germany). 2 micro grams of amplified and purified cDNA were subsequently fragmented with RQ1 RNase-Free DNase (Promega Corp., Fitchburg, Wis., U.S.A.) and labeled with biotinylated deoxynucleoside triphosphates by Terminal Transferase (Roche Diagnostics Corp., Indianapoli, Ind., U.S.A.) and GeneChip® DNA Labeling Reagent (Affymetrix Inc., Santa Clara, Calif., U.S.A). The labeled cDNA was hybridized onto the GeneChip HG U133 Plus 2.0 Array (Affymetrix) in a Hybridization Oven 640 (Agilent Technologies) at 60 rotations per minute, 50° C. for 18 hours. The HG U133 Plus 2.0 Array contains 54,675 probe sets representing approximately 39,000 best-characterized human genes. After hybridization, the arrays were washed and stained according to the Affymetrix protocol EukGE-WS2v4 using a GeneChip® Fluidics Station 450 (Affymetrix). The arrays were scanned with the GeneChip® Scanner 3000 (Affymetrix).

3. Statistical Analysis

Microarray data quality control was performed according to the suggestions of standard Affymetrix quality control parameters. The Affymetrix expression arrays were preprocessed globally by Robust Multi-chip Average method (RMA) with background correction, quantile normalization and median polish summarization (Irizarry R A et al., Biostatistics 20 3; 4:249-64).

For cohort 1 data, the probesets with extreme signal intensity (lower than log 2 (50) or higher than 2E14) were filtered out. Then, biological knowledge based filtering were performed using the information of Entrez Gene Database (Maglott D et al., Nucleic Acids Research 2007; 35:D26-31). Probesets without Entrez Gene ID annotation were removed. For multiple probesets mapping to the same Entrez Gene ID, only the probeset with the largest value of Inter Quantile Range were retained and the others were removed. After two-steps filtering, 9,859 probesets were kept for the downstream analysis. To reduce the likelihood of batch effect, Combat method was applied to the filtered expression data (Johnson W E et al., Biostatistics 2007; 8:118-27). Differentially Expressed Gene (DEG) analysis was performed by the Significance Analysis of Microarrays (SAM) method (False Discovery Rate=0.05; Type="Two class unpaired"; test statistic="t-statistic"; number of permutations=1,000) (Tusher V G et al., PNAS USA 2001, 98:5116-21). Significant gene selection and predictive model construction were performed using a 5-fold cross validation process with RFE-SVM method. Among the 200 samples in train set, 160 were randomly selected to form a learning set; the predictive models were created with the different sizes ranging from 1 to 100 genes scored by RFE-SVM; and the model performance was assessed using the rest of 40 samples. This process was repeated 1,000 times. Our result suggested that a maximum 97% accuracy was achievable with the 100-gene based SVM predictive models. The signature size optimization took into account the prediction performance, signature complexity and economy. Finally, we identified seven core genes with overall 90% accuracy to meet our target performance. The seven genes were selected by t-test P value, fold change, biological function and not related to age or gender factors.

II) Results

1. Characteristics of the Colorectal Cancer and Control Patient Populations

Among 309 participants in the two cohorts, there were 161 CRC patients and 148 CNCs. The demographic and clinical characteristics of the patients are summarized in the table 1.

TABLE 1

Clinical characteristics of the Patients

| | Train set | | Test set | |
|---|---|---|---|---|
| Variable | CRC (n = 100) | Control (n = 100) | CRC (n = 61) | Control (n = 48) |
| Age - yr | | | | |
| Mean | 57.6 | 56.5 | 55.4 | 55.2 |
| Range | 27-78 | 38-74 | 34-82 | 38-70 |
| Sex - no. (%) | | | | |
| Male | 50 (50.0%) | 50 (50.0%) | 32 (52.5%) | 3 (6.3%) |
| Female | 50 (50.0%) | 50 (50.0%) | 29 (47.5%) | 45 (93.7%) |
| Tumor site - no. (%) | | | | |
| Colon | 41 (41.0%) | — | 33 (54.1%) | — |
| Rectum | 59 (59.0%) | | 28 (45.9%) | |
| Stage I | 16 (16.%) | | 8 (13.1)% | |
| Stage II | 36 (36.0%) | — | 19 (31.1%) | — |
| Stage III | 24 (24.0%) | | 17 (27.9%) | |
| Stage IV | 24 (24.0%) | | 17 (27.9%) | |

2. 7-Gene CRC Biomarker Panel: Identification and Validation

Train set: the inventors performed significant gene selection and prediction model construction based on 5-fold cross validation process. The process was run for 1,000 iterations. Within each iteration, they recorded the unique top-7 gene set and its corresponding prediction model performance accessed by internal test fold. Eventually, the overall performance was estimated by taking the average performance of 1,000 prediction models in the internal test fold. The results show that an overall accuracy performance of 90.0% is achievable with prediction models. The inventors have selected the best 7-gene prediction model, for which 90.0% accuracy, 89.0% sensitivity and 91.0% specificity for the train set.

Test set: the inventors have then verified the performance of the signature of the above prediction model identified in the train set in an independent cohort (test set) including 109 samples, 61 CRCs and 48 CNCs. The overall performance of this signature are 83.0% (CI %:73.9, 88.9) accuracy, 84.0% (CI %:71.5, 91.4) sensitivity, and 81.0% (CI %:66.9, 86.6) specificity.

3. Analysis of Discriminative Capacities of Individual Genes from the Signature Observed from the Train Set.

The table 2 below summarizes the individual performance of said 7 genes. For each gene are given the individual characteristics like Probeset_id (Affymetrix probeset identification), T_test P value observed between 100 CNCs and 100 CRCs, and Fold Change observed between 100 CNCs and 100 CRCs.

TABLE 2

| Probeset_id* | Gene Symbol** | SEQ ID NOs: | Mean signal*** | t-test P value | Fold Change | Direction (in CRC) |
|---|---|---|---|---|---|---|
| 227062_at | NEAT1 | 1 | 621 | $3.84\ 10^{-11}$ | 1.46 | up |
| 223204_at | FAM198B | 2, 3, 4 | 97 | $3.56\ 10^{-12}$ | 1.52 | up |
| 205785_at | ITGAM | 5, 6 | 95 | $1.35\ 10^{-17}$ | 1.32 | up |
| 213906_at | MYBL1 | 7, 8 | 139 | $3.51\ 10^{-8}$ | 1.38 | down |
| 209339_at | SIAH2 | 9 | 252 | $8.06\ 10^{-6}$ | 1.25 | up |
| 1553589_a_at | PDZK1IP1 | 10 | 407 | $9.32\ 10^{-5}$ | 1.37 | down |
| 1553991_s_at | VSIG10 | 11 | 65 | $1.47\ 10^{-14}$ | 1.41 | up |

Up: means that the mean signal for the CRC group is higher than in the CNC group Down means that the mean signal for the CRC group is lower than for CNC group

*means Probeset_id according to Affymetrix annotation version in 2010 (https://www.affymetrix.com/analysis/netaffx/xmlquery.affx?netaffx=netaffx4_annot&_requested=403680)

**means the identified gene and its variants or related sequences to said gene or variants

***means average signals observed for 100 CRCs and 100 CNCs array experiments

The invention claimed is:

1. A method comprising:

measuring an amount of at least one expression product expressed from at least one target gene selected from the group consisting of the FAM198B, MYBL1, PDZK11P1, and VSIG10 genes, wherein the amount of the expression product is measured using a peripheral blood sample obtained for in vitro colorectal cancer testing from an individual.

2. The method of claim 1, wherein the amount of the expression product is measured by an assay that comprises contacting the expression product with at least one binding partner specific for the expression product.

3. The method of claim 1, comprising measuring the amounts of a plurality of expression products expressed from a plurality of target genes selected from the group consisting of the FAM198B, MYBL1, PDZK11P1, and VSIG10 genes, wherein the amounts of the expression products are measured by an assay that comprises contacting the expression products with binding partners specific for the expression products.

4. The method of claim 1, wherein the amounts of fewer than 50 expression products are measured.

5. The method of claim 1, comprising measuring the amounts of expression products expressed from the NEAT1, FAM198B, ITGAM, MYBL1, SIAH2, PDZK11P1, and VSIG10 genes.

6. The method of claim 1, wherein the expression product is an RNA transcript or a polypeptide.

7. The method of claim 1, wherein the amount of the expression product is measured using at least one of hybridization, amplification, or sequencing.

8. The method of claim 1, wherein the expression product is mRNA that is hybridized with at least one probe, at least one primer, or a combination thereof.

9. The method of claim 1, wherein cDNA of the expression product is hybridized with at least one probe, at least one primer, or a combination thereof.

10. The method of claim 1, wherein cRNA of the expression product is hybridized with at least one probe, at least one primer, or a combination thereof.

11. The method of claim 1, wherein the expression product is a polypeptide that is bound by at least one ligand specific for the polypeptide.

12. The method of claim 11, wherein the ligand is an antibody.

13. The method of claim 11, wherein the ligand is an affinity protein.

14. The method of claim 11, wherein the polypeptide is bound by at least two ligands specific for the polypeptide.

15. A kit for in vitro colorectal cancer testing, comprising:

one or more binding partners specific for from 1 to no more than 50 expression products that include at least one binding partner specific for an expression product expressed from a target gene selected from the group consisting of the FAM198B, MYBL1, PDZK11P1, and VSIG10 genes, wherein the binding partner is attached to a detectable label or solid substrate.

16. The kit of claim 15, further comprising instructions for performing in vitro colorectal cancer testing using a peripheral blood sample obtained from an individual.

17. The kit of claim 15, comprising a plurality of binding partners specific for a plurality of expression products expressed from a plurality of target genes selected from the group consisting of the FAM198B, MYBL1, PDZK11P1, and VSIG10 genes.

18. The kit of claim 15, comprising a combination of binding partners specific for the expression products expressed from the NEAT1, FAM198B, ITGAM, MYBL1, SIAH2, PDZK11P1, and VSIG10 genes.

19. The kit of claim 15, wherein the one or more binding partners include at least one hybridization probe.

20. The kit of claim 15, wherein the one or more binding partners include at least one hybridization probe and at least one primer.

21. The kit of claim 15, wherein the one or more binding partners include at least one hybridization probe and a pair of primers.

22. The kit of claim 15, wherein the one or more binding partners include at least one ligand.

23. The kit of claim 15, wherein the one or more binding partners include at least one antibody or affinity protein.

24. The kit of claim 15, wherein the one or more binding partners include at least two ligands specific for the same expression product.

25. The method of claim 1, further comprising measuring an amount of at least one expression product expressed from at least one of the NEAT1, SIAH2, and ITGAM target genes.

26. A method comprising:

measuring amounts of a plurality of expression products expressed from (i) at least one of the NEAT1 and ITGAM target genes, and (ii) at least one target gene selected from the group consisting of the FAM198B, MYBL1, SIAH2, PDZK11P1, and VSIG10 genes, wherein the amounts of the expression products are measured using a peripheral blood sample obtained for in vitro colorectal cancer testing from an individual.

27. A method comprising:

measuring amounts of a plurality of expression products expressed from a plurality of target genes selected from the group consisting of the FAM198B, MYBL1, SIAH2, PDZK11P1, and VSIG10 genes, wherein the amounts of the expression products are measured using a peripheral blood sample obtained for in vitro colorectal cancer testing from an individual.

* * * * *